(12) United States Patent
Caplice

(10) Patent No.: US 8,470,596 B2
(45) Date of Patent: Jun. 25, 2013

(54) PRIMITIVE VASCULAR PROGENITOR CELLS AND USES THEREOF

(75) Inventor: Noel Caplice, Co. Cork (IE)

(73) Assignee: University College Cork, National University of Ireland, Cork (IE)

( * ) Notice: Subject to any disclaimer, the term of this patent is extended or adjusted under 35 U.S.C. 154(b) by 0 days.

(21) Appl. No.: 13/001,880

(22) PCT Filed: Jun. 30, 2009

(86) PCT No.: PCT/IE2009/000041
§ 371 (c)(1),
(2), (4) Date: Dec. 29, 2010

(87) PCT Pub. No.: WO2010/001375
PCT Pub. Date: Jan. 7, 2010

(65) Prior Publication Data
US 2011/0110853 A1    May 12, 2011

Related U.S. Application Data

(60) Provisional application No. 61/076,760, filed on Jun. 30, 2008.

(30) Foreign Application Priority Data

Jun. 30, 2008  (EP) .................................... 08159371

(51) Int. Cl.
*C12N 5/00* (2006.01)
*A01N 63/00* (2006.01)

(52) U.S. Cl.
USPC ........................................ 435/325; 424/93.21

(58) Field of Classification Search
CPC ................................. A61K 38/00; A61K 48/00
USPC ........................................ 435/325; 494/93.21
See application file for complete search history.

(56) References Cited

FOREIGN PATENT DOCUMENTS
WO        2008/054319        5/2008

OTHER PUBLICATIONS

Laugwitz, K. et al., Development, 135(2):193-205 (2008). "Islet1 cardiovascular progenitors: a single source for heart lineages."
Metharom et al., Atherosclerosis, 198(1):29-38 (2007). "Myeloid lineage of high proliferative potential human smooth muscle outgrowth cells circulating in blood and vasculogenic smooth muscle-like cells in vivo."
Moretti, A. et al., Cell, 127(6)1151-1165 (2006). "Multipotent embryonic Isl1(+) progenitor cells lead to cardiac, smooth muscle, and endothelial cell diversification."
Simper, D. et al., Circulation, 106(10):1199-1204 (2002) "Smooth muscle progenitor cells in human blood."

*Primary Examiner* — Marcia S. Noble
(74) *Attorney, Agent, or Firm* — Nixon Peabody LLP; David S. Resnick; Leena H. Karttunen Contarino

(57) ABSTRACT

Described herein are isolated mammalian cells (progenitor cell biomarkers), referred to as primitive vascular progenitor cells (PVPC), which are present in and isolated from blood (e.g., peripheral blood) and useful as biomarkers of vascular remodeling in mammals (e.g., humans, rodents).

4 Claims, 11 Drawing Sheets

*: p < 0.05

PRIMITIVE VASCULAR PROGENITOR CELLS AND USES THEREOF

CROSS REFERENCE TO RELATED APPLICATIONS

This application is a 371 National Phase Entry Application of International Application No. PCT/IE2009/000041 filed Jun. 30, 2009, which designates the U.S., and which claims the benefit of priority under 35 U.S.C. § 119(e) of U.S. Provisional Application No. 61/076,760 filed Jun. 30, 2008 and also claims the benefit of priority of European Patent Application No. 08159371.7 filed Jun. 30, 2008, the contents of which are incorporated herein by reference in their entirety.

BACKGROUND OF THE INVENTION

Atherosclerotic cardiovascular disease is a leading cause of mortality in the United States. Better methods and reagents for its diagnosis and treatment are badly needed.

SUMMARY OF INVENTION

Described herein are unipotent mammalian cells, which are present in blood (e.g., peripheral blood, such as adult peripheral blood); exhibit Islet-1 (Isl-1), the encoded product (referred to as Isl-1 protein) of an ISLET-1 (ISL-1) gene; and are useful as biomarkers (are progenitor cell biomarkers) of vascular remodeling in mammals (e.g., humans, rodents). Such cells are referred to herein as primitive vascular progenitor cells (PVPC). PVPC can be read in the singular (primitive vascular progenitor cell) or in the plural (primitive vascular progenitor cells).

As used herein, the term "isolated PVPC" refers to isolated unipotent mammalian cells, which themselves or an ancestor thereof were isolated (removed or separated) from mammalian (e.g., human) blood (such as peripheral blood, such as adult human peripheral blood); exhibit Isl-1 and, optionally one or more additional markers described herein; and are biomarkers for vascular remodeling and, in particular, for vascular disease.

PVPC that are unipotent and exhibit Isl-1 and present in bone marrow are referred to herein as "bone-marrow-derived PVPC." The term "isolated bone-marrow-derived PVPC" refers to isolated unipotent mammalian cells, which themselves or an ancestor thereof were isolated from mammalian (e.g., human) bone marrow.

The PVPC described herein are biomarkers of vascular remodeling and, thus, are useful as biomarkers of any condition in which vascular remodeling occurs, such as vascular disease. Examples of vascular disease for which the PVPC can be used as biomarkers include, but are not limited to, atherosclerosis, peripheral vascular disease, pulmonary vascular disease, pulmonary hypertension, renovascular hypertension, occlusive vascular disease, restenosis, and coronary heart disease.

In certain embodiments, methods are provided for detecting, in a human, a unipotent cell that exhibits Isl-1, the method comprising determining if a cell that exhibits Isl-1 is present in peripheral blood obtained from the human. In certain embodiments, the human is an adult. In certain embodiments, the unipotent cell that exhibits Isl-1 in the adult peripheral blood is a biomarker of vascular remodeling.

A biomarker, as the term is used herein, is an indicator that can be detected or measured (for example in a sample (e.g., peripheral blood) obtained from an individual, such as a human) in which the detected absence or presence or measured quantity correlates with or can be used to determine (for example): i) the risk or likelihood that an individual will develop a condition in which vascular remodeling occurs, and/or ii) the extent to which an individual has or suffers from a condition in which vascular remodeling occurs. A biomarker can be, for example, a cell (e.g. PVPC) or a nucleic acid or protein (e.g. Isl-1) that is exhibited by the cell and can be used to identify the cell.

For example, in certain embodiments, the absence or presence of PVPC in the peripheral blood of an adult mammal (e.g., human) and/or the number or amount of PVPC found in a peripheral blood sample obtained from the adult mammal (in which the number of PVPC may be determined, e.g. by the relative gene expression of ISL-1 or relative Isl-1 protein expression) is an indicator (or biomarker): i) that the mammal has or is at risk of developing a condition in which vascular remodeling occurs, and/or ii) for the likelihood that the mammal will develop a condition in which vascular remodeling occurs, and/or iii) for the extent to which the mammal suffers from a condition in which vascular remodeling occurs. In each instance, the mammal can be an adult human.

As is discussed herein, unipotent mammalian cells that exhibit Isl-1 described herein can be identified or defined by additional characteristics, such as expression of additional markers, population doublings and/or the lineage(s) into which they differentiate.

In one embodiment, PVPC exhibit Is1-1.

In another embodiment, PVPC, in addition to Isl-1, also exhibit Oct-4.

In another embodiment, PVPC, in addition to Isl-1, also exhibit Flk-1.

In another embodiment, PVPC, in addition to Isl-1, also exhibit Oct-4 and Flk-1.

In further embodiments, PVPC optionally additionally exhibit a (at least one, one or more) smooth muscle cell marker, such as one or more of the following smooth muscle cell markers: smooth muscle actin (SMA), myosin heavy chain (c-MHC), calponin and smoothelin (SMTH).

For example, in one embodiment PVPC exhibit Isl-1 and a (at least one, one or more) smooth muscle cell marker: smooth muscle actin, myosin heavy chain, calponin and/or smoothelin. In another embodiment PVPC exhibit Isl-1 and Oct-4 and a (at least one, one or more) smooth muscle cell marker: smooth muscle actin, myosin heavy chain, calponin and/or smoothelin. In another embodiment PVPC exhibit Isl-1 and Flk-1 and a (at least one, one or more) smooth muscle cell marker: smooth muscle actin, myosin heavy chain, calponin and/or smoothelin. In another embodiment PVPC exhibit Isl-1, Oct-4, Flk-1 and a (at least one, one or more) smooth muscle cell marker: smooth muscle actin, myosin heavy chain, calponin and/or smoothelin.

The subject isolated mammalian cells (isolated PVPC) are typically capable of exceeding the Hayflick limit of population doublings (about 70 population doublings) in vitro. For example, in some embodiments, isolated PVPC are capable of undergoing at least 70 population doublings in vitro, at least 100 population doublings in vitro, at least 150 population doublings in vitro, and/or at least 250 population doublings in vitro.

In some embodiments, the isolated mammalian cells (isolated PVPC) described herein exhibit telomerase activity greater than that of normal vascular smooth muscle cells in vitro. For example, such isolated PVPC exhibit telomerase activity that is twice (two-fold), three-fold or four-fold the telomerase activity of normal vascular smooth muscle cells.

Isolated PVPC have been shown to be unipotent, under the conditions described herein. In certain embodiments, the isolated PVPC do not differentiate into endothelial cell lineages under in vitro conditions favoring such differentiation (e.g., under conditions described herein under the heading endothelial cell differentiation method).

In other embodiments, the isolated PVPC do not differentiate into cardiomyocyte lineages under in vitro conditions favoring such differentiation (e.g., under conditions described herein under the heading cardiomyocyte differentiation method).

PVPC of any of the embodiments described herein can be circulating cells in the peripheral blood of a variety of adult mammals and isolated PVPC or an ancestor thereof can be isolated from peripheral blood of a variety of adult mammals, such as a rodent, a pig or a human. In certain embodiments the adult mammal is an adult human.

PVPC described herein are a biomarker of vascular remodeling. In certain embodiments, PVPC in the peripheral blood of an adult mammal, for example, an adult human, are a biomarker for vascular remodeling.

PVPC described herein are not detectable, under the conditions (using detection methods) described herein, in peripheral blood of adult mammals (e.g., adult humans) who do not have a condition in which vascular remodeling occurs. For example, this is the case when a colony forming assay, such as described herein, is used to assess a blood sample for PVPC, under the conditions described herein. When cells from peripheral blood from adult mammals (humans) who do not have a condition in which vascular remodeling occurs are isolated and tested under in vitro conditions measuring the ability of the cells to grow, e.g. in a colony forming assay, no cell outgrowth of PVPC is detected.

In certain embodiments, PVPC in the peripheral blood of a mammal (e.g., an adult human mammal) indicate that there is an underlying condition involving vascular remodeling in the mammal (such as an adult human) and a PVPC is a biomarker useful in (aiding) the determination of an underlying condition involving vascular remodeling in the adult mammal (e.g., adult human).

Also described herein is a method of predicting or aiding in predicting the likelihood that an individual (e.g., a human, such as an adult human) will develop vascular disease, comprising determining whether PVPC described herein are present in the peripheral blood of the individual, wherein if the biomarker is present in the peripheral blood, the individual is more likely to develop vascular disease than if the biomarker is not present in peripheral blood.

In the methods described herein, the presence of the PVPC is determined, for example, using (a) antibodies specific for the detection of Isl-1 protein, antibodies specific for Oct-4 protein or both antibodies specific for Isl-1 protein and antibodies specific for Oct-4 protein or (b) nucleic acid probes or primers specific for the detection of ISL-1 nucleic acids, such as, for example, ISL-1 mRNA, or nucleic acid probes or primers specific for OCT-4 nucleic acids, such as, for example, OCT-4 mRNA, or both nucleic acid probes or primers specific for the detection of ISL-1 nucleic acids and nucleic acid probes or primers specific for OCT-4 nucleic acids.

The methods can further comprise determining the presence of Flk-1 in PVPC present in a blood sample obtained from an individual using (a) antibodies specific for the detection of Flk-1 protein or (b) nucleic acid probes or primers specific for the detection of FLK-1 nucleic acids, such as, for example, FLK-1 mRNA.

The methods can further comprise determining one or more (at least one) of the following characteristics of PVPC: population doubling potential, telomerase activity, expression of smooth muscle actin, expression of myosin heavy chain, expression of calponin and expression of smoothelin.

In certain embodiments, the methods described herein further comprise (a) partially purifying cells from the blood; and (b) analyzing cells partially purified in (a) for the presence of Isl-1. In certain embodiments, the presence of Isl-1 is determined by measuring Isl-1 mRNA or Isl-1 protein level in a sample. In certain embodiments, the methods further comprise detecting Oct-4 mRNA or Oct-4 protein. In certain embodiments, the methods further comprise detecting Flk-1 mRNA or Flk-1 protein in the sample. In certain embodiments, the methods further comprise detecting mRNA or protein from one or more additional markers characteristic of smooth muscle cells selected from the group consisting of smooth muscle actin (SMA), myosin heavy chain (MHC), calponin, and smoothelin.

The methods can further comprise determining one or both of the following characteristics of PVPC present in a blood sample obtained from an individual: inability to differentiate into endothelial lineages under conditions that favor differentiation in vitro described herein and/or inability to differentiate into cardiomyocyte lineages, under conditions favoring differentiation in vitro described herein. For example, these characteristics can be determined, respectively, through the use of the endothelial cell differentiation method and the cardiomyocyte differentiation method described herein.

Also described herein is a method of determining the extent to which an adult individual (human) exhibits vascular remodeling and, in certain embodiments, suffers from vascular disease, comprising determining, in a sample obtained from the individual (e.g., a peripheral blood sample), the level of PVPC (e.g., determining the level of cells that exhibit Isl-1 and, optionally, exhibit/express additional markers, such as Oct4, and/or Flk-1, and/or a smooth muscle cell marker(s)), wherein the higher the level of the biomarker (PVPC), the greater the extent to which the individual has vascular disease. In the method, the level of cells that exhibit Isl-1 and, optionally, other markers, such as Oct4 is determined using (a) antibodies specific for the detection of Isl-1 protein, or antibodies specific for Oct-4 protein or both antibodies specific for Isl-1 protein and antibodies specific for Oct-4 protein or (b) nucleic acid probes or primers specific for the detection of ISL-1 nucleic acids, such as, for example, ISL-1 mRNA, or nucleic acid probes or primers specific for OCT-4 nucleic acids, such as, for example, OCT-4 mRNA, or both nucleic acid probes or primers specific for the detection of ISL-1 nucleic acids and nucleic acid probes or primers specific for OCT-4 nucleic acids. The sample can be a blood sample, such as a peripheral blood sample.

The method can further comprise determining the levels of additional markers, such as Flk-1, and/or a smooth muscle cell marker(s) (smooth muscle actin, myosin heavy chain, calponin and/or smoothelin) using protein specific antibodies or gene specific nucleic acid probes or primers.

In certain embodiments, determining the level of expression of Isl-1, as measured, for example by Isl-1 mRNA levels, in a sample, such as a peripheral blood sample, aids in determining the extent to which an individual exhibits vascular remodeling or suffers from vascular disease. A high level of Isl-1 expression in a sample is indicative of or can be correlated with a greater extent to which the individual exhibits a condition in which vascular remodeling occurs. A high level of Isl-1 expression in a sample, in certain embodiments, is measured by Isl-1 mRNA levels using, for example qRT-PCR. In these embodiments, the level of mRNA is 1, 2, 3, 4, 5, 6, 7, 8, 9, 10 or more logs (log 10) higher than Isl-1 expression (mRNA levels) detected in a control sample of an individual not exhibiting vascular disease.

As described herein, isolated PVPC are capable of recapitulating vascular disease (such as atherosclerosis or pulmonary hypertension, alone or in combination) in a non-human mammal when such a cell is adoptively transferred in sufficient numbers into the mammal (into a mammal "primed" or subjected to injury in order to develop vascular disease, such as atherosclerosis). For example, isolated mammalian cells described herein are capable of recapitulating vascular disease in a non-human mammal in which there are one or more vessel injuries. The non-human mammal can be any in which adoptive transfer can be carried out and will be, for example, a rodent (e.g., mouse, rat) or a pig.

One embodiment described herein is a model of vascular disease, wherein the model comprises a non-human mammal in which vascular disease is produced by adoptive transfer in vivo of isolated mammalian cells (isolated PVPC) described herein into the non-human mammal in amounts sufficient for recapitulation of vascular disease in the mammal. In certain embodiments, the mammal has one or more vessel injuries. The vascular disease can be, for example, atherosclerosis or pulmonary hypertension, alone or in combination. The non-human mammal can be any in which adoptive transfer can be carried out and will be, for example, a rodent (e.g., mouse, rat) or a pig.

Also described herein is an in vivo method of identifying an agent that reduces vascular disease, comprising administering, to a non-human model, such as an animal model described herein, a candidate agent and assessing vascular disease in the model, wherein if vascular disease occurs to a lesser extent in the animal model to which the candidate agent is administered than when the candidate agent is not administered, the candidate agent is an agent that reduces vascular disease. In one embodiment, the method is carried out in a model of vascular disease, wherein the model comprises a non-human mammal in which vascular disease is produced by adoptive transfer in vivo of isolated mammalian cells (isolated PVPC) described herein into the non-human mammal in amounts sufficient for recapitulation of vascular disease in the mammal. In certain embodiments, the mammal has one or more vessel injuries. The vascular disease can be, for example, atherosclerosis or pulmonary hypertension, alone or in combination. The non-human mammal can be any in which adoptive transfer can be carried out and will be, for example, a rodent (e.g., mouse, rat) or a pig.

A further embodiment described herein is a method of preventing or reducing a condition in which vascular remodeling occurs, such as vascular disease, in a mammal (e.g., a human), comprising blocking or killing cells that exhibit Isl-1 and are biomarkers of vascular disease in the mammal, thereby reducing the number of such cells, their activity or both in the mammal, whereby vascular disease in the mammal is reduced. In one embodiment, the method is carried out by blocking or killing PVPC described herein. For example, PVPC are killed by contacting them with a PVPC specific antibody or fragment thereof coupled to a cytotoxic agent. PVPC-specific antibodies can be directed against signaling molecules (e.g., cell surface receptors), cell adhesion molecules (e.g., integrins) transmembrane glycoproteins, and/or other specific markers, such as CD (cluster of differentiation) markers. The antibody is typically monoclonal. The cytotoxic agent can be, for example, a radionuclide, a chemical toxin, or a protein toxin. One or more (a combination of) cytotoxic agents can be used in the present method. In one embodiment of the method, the PVPC is killed by contact with Fas-ligand. Blocking or killing of PVPC can be carried out by administering to the mammal (e.g., a human) a drug that reduces the activity of such cells, a drug that reduces the number of such cells, or both.

Alternatively, the method of preventing or reducing a condition in which vascular remodeling occurs, such as vascular disease, in an individual is carried out by blocking migration or homing of the PVPC to sites of vessel injury, such as by administering an agent that interferes with its movement, such as by contacting the PVPC with an antibody that binds PVPC and/or is specific for PVPC or a marker thereon or fragment thereof in vivo. For example, the antibody or fragment thereof binds to, blocks or inactivates one or more molecules exhibited by PVPC or expressed on the PVPC cell to surface. For example, the one or more molecules expressed on the cell surface of the PVPC can be cell adhesion molecules or signaling molecule receptors and at least one antibody or fragment thereof that binds to the cell adhesion molecule, at least one antibody or fragment thereof that binds to the signaling molecule or a combination thereof are administered to an individual in need of having vascular disease prevented or reduced. Alternatively, migration or homing of the progenitor cell biomarker to sites of vessel injury is blocked by contacting PVPC with a progenitor cell biomarker-specific siRNA, antisense molecule, ribozyme or any combination thereof in vivo. In specific embodiments, contacting PVPC with the specific siRNA, antisense molecule, or ribozyme destroys or blocks translation of one or more messenger RNA molecules responsible for expression of cell surface molecules (e.g., cell adhesion molecules or signaling molecule receptors) of the PVPC. In another embodiment of the method, migration or homing of the progenitor cell biomarker to the sites of vessel injury is blocked by suppressing or altering cytokine expression of PVPC or of the cells present at sites of vessel injury. In yet another embodiment, migration or homing of PVPC to the sites of vessel injury is blocked by suppressing or altering cell surface molecule expression of the cells present at sites of vessel injury.

Described herein is a method of reducing the extent to which a condition in which vascular remodeling occurs, such as vascular disease, occurs in a human, comprising treating the human in such a manner that cells that exhibit Isl-1 and are biomarkers of vascular disease in the human are reduced in number or function, thereby reducing the ability of the cells to cause vascular disease in the human and the extent to which vascular disease occurs in the human.

Also described herein is a method of identifying an agent that inhibits unipotent cells that exhibit Isl-1 and are biomarkers of a condition in humans in which vascular remodeling occurs, such as vascular disease in humans, comprising (a) contacting a candidate agent with unipotent cells that exhibit Isl-1 and are such biomarkers of vascular disease in humans; (b) assessing activity of cells contacted with the candidate agent; (c) comparing the activity determined in (b) with activity of control cells that exhibit Isl-1 and are biomarkers of vascular disease in humans and are maintained under the same conditions as the conditions of (a) but in the absence of the candidate agent; and (d) determining if there is a difference in activity of cells contacted with the candidate agent and activity of control cells, wherein if activity of cells contacted with the candidate agent is less than activity of cells maintained in the absence of the candidate agent, the candidate agent is an agent that inhibits cells that exhibit Isl-1 and are biomarkers of vascular disease in humans. Contacting the candidate agent with unipotent cells that exhibit Isl-1 and are biomarkers of vascular disease in humans can be carried out in vitro or in vivo. In instances in which contacting is carried out in vivo, it can be carried out using any of the models of vascular disease described herein. For example, it can be carried out under conditions appropriate for developing the disease.

Also described herein are compositions for preventing or reducing a condition in which vascular remodeling occurs, such as vascular disease, in a mammal (e.g., an adult human), comprising (a) one or more agents that block, inhibit or kill cells that exhibit Is1-1 and are cell biomarkers of vascular disease in the mammal (PVPC) and are causative of vascular disease in the mammal and (b) a therapeutically acceptable carrier. The one or more agents that block, inhibit or kill the progenitor cell biomarker are selected from the group consisting of PVPC-specific siRNA, antisense molecule, ribozyme, targeting peptide, or antibody or fragment thereof, such as PVPC-specific siRNA, antisense molecule, or ribozyme that destroys or blocks translation of one or more messenger RNA molecules responsible for expression of cell surface molecules of the progenitor cell biomarker. In one embodiment of the composition, the PVPC-specific antibody or fragment thereof binds to, blocks or inactivates one or more molecules exhibited by or expressed on the cell surface of the PVPC. The one or more molecules expressed on the cell surface of the PVPC can be cell adhesion molecules or signaling molecule receptors. In the composition, the antibody (e.g., a monoclonal antibody) or fragment thereof can be coupled to a cytotoxic agent, which can be, for example, a radionuclide, a chemical toxin, or a protein toxin. One or more agents in the claimed composition that block, inhibit or kill the progenitor cell biomarker described herein (PVPC) are selected from the group consisting of Fas-ligand, cytokine blocking agent, and agents that suppress or alter cell surface molecule expression of the cells present at sites of vessel injury.

A further embodiment is a method for treating or preventing a condition in which vascular remodeling occurs, such as vascular disease, in an individual in need thereof, comprising administering a composition described herein to the individual in an amount sufficient to treat or prevent vascular disease.

These and other aspects of the invention, as well as various advantages and utilities will be more apparent with reference to the drawings and detailed description of the invention.

DETAILED DESCRIPTION OF THE INVENTION

Figure 1:
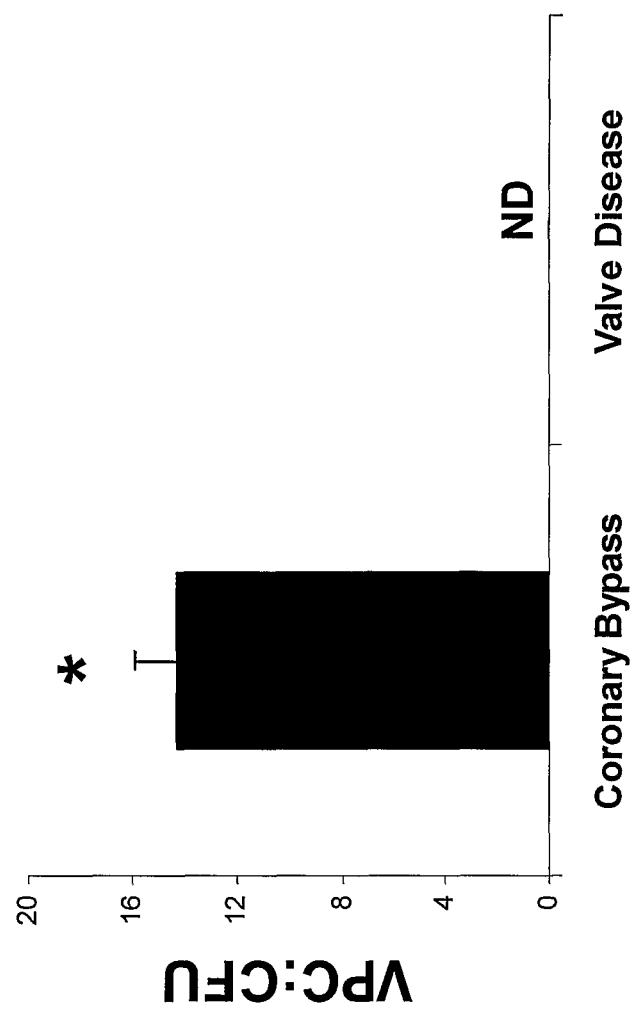
FIG. 1 depicts PVPC colony formation of PVPC isolated from bypass filters of patients with coronary disease and from filters of matched patients undergoing valve surgery without coronary artery disease. (A) A photograph depicting PVPC colonies. (B) A bar graph depicting the number of colony forming units.
Figure 1:
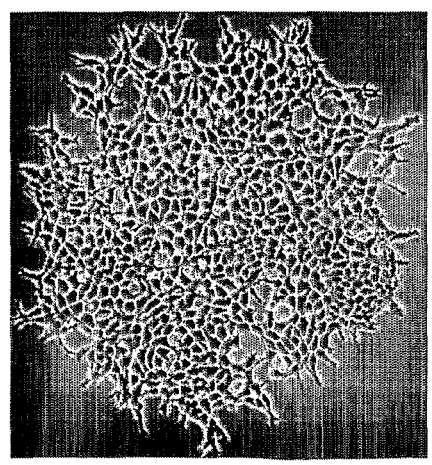

PVPC described herein are unipotent mammalian cells that exhibit Isl-1 and progenitor cells, referred to as PVPC, that can be isolated from peripheral blood of a mammal (e.g., a human or rodent) and in certain embodiments, when adoptively transferred in vivo, recapitulate vascular disease, such as atherosclerosis and pulmonary hypertension. In certain embodiments, PVPC described herein are implicated in vascular disease and are not only useful biomarkers of [conditions characterized by] vascular remodeling, but also a cause of these conditions. Vascular remodeling, as the term is used herein, refers to any change in the structure of the vascular system, such as occurs in arteries to maintain constant blood flow in the face of increased atherosclerotic mass (e.g., compensatory enlargement of atherosclerotic coronary arteries), in resistance arteries in individuals who have arterial hypertension, after angioplasty, and in other conditions in which vessel (e.g., artery) patency is compromised. It is a fundamental characteristic of diseases such as cancer, atherosclerosis, restenosis after angioplasty and hypertension (systemic and pulmonary). As described herein, such PVPC provide the basis for diagnostic methods and treatment methods and reagents useful for assessing the status of individuals as to development of a condition(s) characterized by vascular remodeling or in which vascular remodeling occurs, such as vascular disease, as well as for treating those suffering from such conditions including vascular disease (e.g., to assess and treat individuals for atherosclerosis and/or pulmonary hypertension). Also described here are methods of diagnosing or monitoring vascular remodeling, such as that which occurs in individuals suffering from or at risk for vascular disease (e.g., atherosclerosis and pulmonary hypertension), and in individuals in whom angioplasty has been done.

Isolated unipotent mammalian PVPC cells described herein include cells isolated from the peripheral blood of a mammal and cells whose ancestors were isolated from the peripheral blood of a mammal. This unipotent progenitor cell, referred to as a primitive vascular progenitor cell (PVPC), is characterized by a gene expression profile that includes the primitive marker gene ISL-1 (ISLET-1). Isolated mammalian PVPC described herein exhibit Isl-1 (the product encoded by ISL-1) in such a manner that it can be detected. PVPC can be identified at least in part on the basis of the occurrence of this biomarker and optionally, by additional (different) markers and characteristics described herein. Isl-1 is an intracellular LIM/homeodomain-containing transcription factor found to be expressed in embryonic heart and vascular cells, in stem cells or stem cell-like progenitor cells, such as cardiogenic stem cells and progenitor cell populations, including those of the pancreas, or the neural crest. However, ISL-1 expression in PVPC is unique among cells circulating in the peripheral blood. A description of the use of Islet-1 as a marker for isolating and generating stem cells can be found in PCT-Patent Application No. WO 2004/070013 or U.S. patent application Ser. No. 10/544,053. PVPC described herein express the ISL-1 encoded gene product, designated Is1-1.

In some embodiments, PVPC described herein also exhibit expression of the primitive marker gene OCT-4. The encoded product (Oct-4) is a homeodomain transcription factor of the POU family, which is involved in the self-renewal of undifferentiated embryonic stem cells and is a key factor in the maintenance of pluripotency. Oct-4 is described, for example, in C. E. Ovitt et al. *Mol. Hum. Reprod.*, 4:1021-31, 1998; H. Niwa et al. *Nature Genetics* 24: 372-376, 2000; and methods for detecting Oct-4 are described, for example, in U.S. Pat. No. 7,101,710.

In some embodiments, PVPC described herein also exhibit Flk-1. Flk-1 is a receptor tyrosine kinase and a receptor for vascular endothelial growth factor (VEGF). Flk-1 is described, for example, in Matthews W. et al. *Proc. Natl. Acad. Sci. USA* 88:9026-9030, 1991, and methods for detecting Flk-1 are described for example in Millauer B. et al. *Cell* 72:835-846, 1993.

The PVPC may additionally express one or more gene(s) characteristic of smooth muscle cells (SMCs), such as smooth muscle actin (SMA), myosin heavy chain (MHC), calponin, and/or smoothelin.

PVPC exhibit stem cell-like or progenitor cell characteristics. For example, PVPC that exhibit the primitive markers Isl-1 and Oct-4 also exhibit increased telomerase activity, are capable of exceeding the Hayflick limit of population doublings in vitro, without entering senescence (Hayflick L. *Exp Cell Res* 37:614-36, 1965) or both exhibit increased telomerase activity and are capable of exceeding the Hayflick limit. In one embodiment, the self-renewal capability of PVPCs exceeds 50 population doublings in vitro. In other embodiments the self-renewal capability exceeds 60, 70, 80, 90, 100, 150, 200, 250, or 300 population doublings in vitro.

PVPC described herein circulating in the peripheral blood is the cause of a disease, such as, for example, vascular disease (e.g., atherosclerosis and pulmonary hypertension), in which vascular remodeling occurs. As a result, such PVPC can be targeted for therapy and provide the basis for methods of treatment of individuals suffering from or at risk of having any condition, such as vascular disease, in which vascular remodeling occurs. As used herein, the term treatment includes prevention of a condition, reduction (partial or complete) in the extent to which the condition occurs or progresses and reversal (partial or complete) of the condition in an individual (e.g., adult human) in need thereof. For example, as used herein, the term treatment includes prevention of vascular disease, reduction (partial or complete) in the extent to which vascular disease occurs or progresses, and reversal (partial or complete) of vascular disease in an individual in need thereof (e.g., in an individual in whom vascular disease is developing, an individual suffering from vascular disease). PVPC can be killed, either directly or indirectly. PVPC can be killed, for example, using molecules that target PVPC (e.g., molecules that specifically target PVPC), such as antibodies or fragments thereof, coupled to cytotoxic agents, which are described elsewhere herein. Alternatively, the cells can be killed indirectly, such as by exploiting signaling pathways that lead to cell death (e.g., necrosis or apoptosis). For example, Fas-ligand (FasL) may be used to kill PVPC through apoptosis, if the PVPC is Fas-bearing. Fas is a death receptor that transmits an apoptosis-inducing signal when activated by its ligand, FasL. Fas-ligand can be administered locally to sites of vessel injury, for example as a small molecule (M. Sata et al., *Proc Natl Acad Sci USA*, 95:1213-1217; Z. Luo et al., *Circulation*, 99:1776-1779, 1999; M. Sata et al. *Arterioscler Thromb Vasc Biol*, 20:309-316, 2000).

Alternatively, treatment can be carried out by interfering with or blocking (partially or completely) the ability of PVPC to migrate or home to sites of vessel injury. This may be achieved, for example, by blocking local cytokines or adhesion molecules at the site of injury, and may target specifically endothelial cells lining the vessel, or other cells (Y. Furukawa, *Circ Res*, 84:306-314, 1999; S. Hayashi, *Circulation*, 102: 1701-1707, 2000). Alternatively, homing molecules and receptors expressed in and displayed by the PVPC may be targeted. Antibodies specific to homing molecules, which could be administered locally, may be employed to block these molecules and block (prevent or reduce) migration and/or homing to the site of injury.

Cell adhesion molecules (CAMs) or homing molecules on PVPC described herein, or on endothelial cells lining the vessel, may be targeted and blocked, as described herein, by therapeutic agents, such as specific antibodies or fragments thereof, which prevent or reduce migration and/or homing of PVPC to the sites of vessel injury. CAMs or homing molecules that may be targeted are, for example, immunoglobulin (IG) superfamily (IgSF CAMs), such as ICAM-1 (Intercellular Cell Adhesion Molecule), VCAM-1 (Vascular Cell Adhesion Molecule), PECAM-1 (Platelet-endothelial Cell Adhesion Molecule), and/or Nectins and nectin-like molecules; integrins, cadherins, and/or selectins, such as E-selectin (endothelial), L-selectin (leukocyte) and P-selectin (platelet), and P-selectin glycoprotein ligand-1 (PSGL-1).

Cytokines that may be blocked at the site of vessel injury to prevent migration and/or homing of the PVPC to the sites of vessel injury, include, but are not limited to, interleukin family members (IL-1, IL-2, IL-3, IL-4, IL-5, IL-6, IL-7, IL-10, IL-12, IL-15), interferon family members (IFN alpha, beta, gamma), tumor necrosis factors (TNF alpha, beta), transforming growth factor beta superfamily (TGF alpha, beta, gamma), granulocyte-macrophage colony stimulating factor (GM-CSF), and granulocyte colony stimulating factor (GCSF).

Unipotent mammalian PVPC that exhibit Isl-1 described herein circulating in the peripheral blood (for example of a human adult) serve as a biomarker for conditions in which vascular remodeling occurs, such as vascular disease (e.g., atherosclerosis) migrating to the sites of active atherosclerosis.

The PVPC may be targeted with antibodies, such as antibodies specific for the PVPC, that are coupled to another component, such as a toxic agent useful for treating a condition (e.g., vascular disease) in which vascular remodeling occurs.

Described herein is a method of diagnosing or aiding in diagnosing conditions characterized by vascular remodeling (conditions in which vascular remodeling occurs), such as vascular disease. In this embodiment, PVPC described herein, which are implicated in vascular disease, are analyzed (e.g., quantified) in a sample obtained from an individual (e.g., adult human) to be assessed for vascular disease. The sample can be, for example, blood, such as a peripheral blood sample. In these embodiments, the PVPC serves as a biomarker for vascular disease. Such a biomarker can be a disease-specific progenitor cell biomarker or a biomarker of vascular disease and an additional disease(s). A further embodiment is a method of assessing whether an individual (e.g., an adult human) is at risk of developing a vascular disease. In the method, a sample (e.g., peripheral blood) is taken from an individual to be assessed. In both embodiments, the blood sample is analyzed for PVPC described herein. An elevated level of PVPC described herein in the blood sample is an indication that vascular remodeling is occurring or has occurred in an individual and that the individual has or is at risk of developing a condition characterized by vascular remodeling, such as vascular disease. For example, if the level of PVPC is higher in a sample obtained from the individual than in an appropriate control (e.g., an individual or population of individuals who do not have vascular disease), the individual has or is at risk of developing vascular disease. Alternatively, if the level of PVPC in the sample obtained from the individual is at or below the level in individuals at reduced risk of developing or in individuals who did not develop vascular disease, the individual is at reduced risk of developing vascular disease. In one embodiment, the determinant may be the quantity of total ISL-1 mRNA (messenger RNA) in the sample. ISL-1 mRNA expression is very low or almost undetectable in peripheral blood from individuals not suffering from vascular disease. If the quantity of ISL-1 message in a sample from an individual being assessed is elevated relative to that of a control (e.g., an individual or group of individuals not suffering from a vascular disease) then the subject is diagnosed as having vascular disease or is determined as being at risk of developing vascular disease. For example, the level of ISL-1 mRNA may be 1, 2, 3, 4, 5, 6, 7, 8, 9, 10 or more logs ($\log_{10}$) higher than ISL-1 mRNA levels detected in the control.

ISL-1 mRNA can be isolated from the cells isolated from the peripheral blood, which contain the PVPC described herein. The PVPC described herein are characterized, at least in part, by expression of ISL-1. ISL-1 mRNA can be detected and quantified by any means known to those of skill in the art. mRNA expression methods include PCR (RT-PCR, qRT-PCR), DNA microarray, Northern blot, nuclease protection assays (NPA), in situ hybridization (ISH), single cell nanoprobe (SCN) method.

For example, this can be done by RT-PCR (Reverse transcriptase-PCR analysis of mRNA), using reverse transcriptase to convert mRNA into complementary DNA (cDNA) which is then amplified by PCR, or preferably using real-time PCR (qRT-PCR). Real-time PCR is combined with reverse transcription polymerase chain reaction (RT) to quantify messenger RNA (mRNA). Its key feature is that the amplified DNA is quantified as it accumulates in the reaction in real time after each amplification cycle. Two common methods of quantification are the use of fluorescent dyes that intercalate with double-strand DNA, and modified DNA oligonucleotide probes that fluoresce when hybridized with a complementary DNA. PCR methods are well known in the art, e.g., Higuchi, R. et al. *Biotechnology*, 10:413-417, 1992; Higuchi, R. et al. *Biotechnology*, 11:1026-30, 1993.

mRNA expression of other biomarkers, such as, for example, OCT-4, FLK-1, SMA, c-MHC, calponin, or smoothelin, can also be detected by the methods described herein for ISL-1 mRNA.

PVPC can be partially purified or isolated (e.g. from blood) and can be analyzed by any methods known in the art. Cell separation methods include lytic removal of cell subsets, complement-based cell lysis, density gradient separations, centrifugal elutriation, biotin avidin immunochromatography, immunoaffinity purification, flow cytometry-based fluorescence-activated cell sorting, and immunomagnetic cell sorting.

For example, the cells contained in the sample of peripheral blood, including the PVPC described herein, can be isolated by any means known in the art. Methods for blood cell fractionation and isolation of total RNA from whole blood, removal of red blood cells, heme, anticoagulants, globin mRNA, and other contaminants to obtain high-quality mRNA purifications are also well known in the art and many purification kits are commercially available, e.g. from Applied Biosystems/Ambion. One exemplary protocol can be found in the Example section.

In certain embodiments, biomarker protein expression is detected. Biomarker protein expression, such as, for example, Isl-1, Oct-4, Flk-1, SMA, c-MHC, calponin, or smoothelin, can be detected by any method known in the art. Protein detection methods include Western blot, ELISA, 1- or 2-dimensional electrophoresis optionally coupled with Mass spectroscopy, e.g. MALDI, MS-MALDI (peptide mass fingerprinting, and/or post-source decay (PSD) analysis), electrospray ionization mass spectrometry, tandem mass spectrometry (ESI-MS/MS), immunofluorescence spectroscopy, fluorescence-activated cell sorting, immunoaffinity chromatography, and protein microarrays. These methods are well known in the art.

In some embodiments, in vitro assays for screening isolated cell lines to develop agents that may influence or alter the behavior of the isolated cell line are provided. The agents used in the screen may be small organic molecules, antibodies, peptides, cyclic peptides, nucleic acids, antisense nucleic acids, siRNAs, sphingolipid analogs, and/or ribozymes, but are not so limited. The provided assays may score alterations in behavior of the cell line being such as, for example, cell proliferation, cell migration, cell homing, release of cytokines and other signaling molecules and/or presentation of cell surface markers. Cell migration may be modulated by modulation of the expression and/or activity of migration molecules such as, for example, EDG molecules, selectins, integrins, cadherins, certain members of the immunoglobulin superfamily of molecules, or chemokine receptor molecules. These cellular characteristics may be score by any means known in the art. In one embodiment the isolated cell lines provided are derived from isolated PVPC described herein. Isolation protocols and in vitro culture conditions for the PVPC described herein are taught herein (see Examples). Modifications to existing protocols to suit particular subpopulations of isolated cells are routine, and well known in the art (e.g. L. S. Ferreira et al. *Circ Res,* 101:286-94, 2007, and U.S. Pat. No. 5,599,703). The PVPC-derived cell lines may be grown in 96- or 384-well plates to allow automation and high-throughput screening (HTS). HTS assays are described for example for cell migration in U.S. patent application Ser. No. 11/166,920, and for cell proliferation in U.S. Pat. Nos. 5,910,403 and 5,972,639 and U.S. patent application Ser. No. 10/473,295. In vitro binding assays to determine changes in homing receptors and/or other cell surface markers influencing, for example cell adhesion, are well known in the art.

Reporter genes, such as, for example, luciferase, green fluorescent protein (GFP), or β-galactosidase, can be transfected into the isolated PVPC cell lines provided, by methods well known in the art. Transfection methods include, but are not limited to, non-viral transfection systems, such as calcium phosphate tranfection, DEAE-Dextran tranfection, electroporation and liposomal tranfection (e.g., LIPOFECTIN or LIPOFECTAMINE from Invitrogen, or DOTAP from Roche), as well as viral transfection methods, e.g., using retroviral systems such as based on lentiviruses or adenoviruses. The reporter genes may be fused to one or more promoter elements of the ISL-1 promoter and transfected into the PVPC cell lines provided (see e.g., Examples).

In certain embodiments, animal models for adoptive transfer of vascular disease are provided. In certain embodiments, animals, such as, for example, rats, mice, rabbits or pigs, may be primed for adoptive transfer by causing arterial trauma and endothelial cell denudation using a balloon injury method to mimic atherosclerosis, as described herein (see, Examples, and U.S. Pat. Nos. 5,283,257; 5,516,781; 5,733,925). The primed animals are then injected with the PVPC described herein, carrying a modified genome, e.g., expressing a promoter-reporter construct. The modified PVPCs can then be followed to sites of vessel injury in vivo, following expression of the reporter gene (see, Examples). PVPC described herein is a causal agent of vascular disease, such as atherosclerosis and pulmonary hypertension; the PVPC recapitulates these two major vascular diseases in vivo in the animal model.

Thus, in vivo therapeutic compound screens can be conducted with these animals, making it possible to screen small organic molecules, antibodies, peptides, cyclic peptides, nucleic acids, antisense nucleic acids, siRNAs, sphingolipid analogs, and/or ribozymes for their effects on in vivo cell proliferation, cell migration or cell homing of the PVPCs provided herein. A compound that negatively affects cell proliferation of the PVPC or prevents PVPC cell migration or cell homing to sites of vessel injury in vivo may alleviate vascular diseases such as atherosclerosis and pulmonary hypertension and hence may be used as therapeutic compounds to treat these diseases.

In certain embodiments cell surface markers, adhesion molecules, or homing molecules of the circulating PVPC described herein or the endothelial cells lining the vessel are targeted by specific antibodies, or fragments thereof, to prevent migration and/or homing of the PVPC to sites of vessel injury.

The antibodies described herein are prepared by any of a variety of methods, including administering a protein, fragments of a protein, cells expressing the protein or fragments thereof and the like to an animal to induce polyclonal antibodies. Monoclonal antibodies to these molecules can be produced according to techniques well known in the art. It is well-known in the art that only a small portion of an antibody molecule, the paratope, is involved in the binding of the antibody to its epitope (see, in general, Clark, W. R., 1986, The Experimental Foundations of Modern Immunology, Wiley & Sons, Inc., New York; Roitt, I., 1991, Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation. Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity. It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762, and 5,859,205. Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans. Thus, as will be apparent to one of ordinary skill in the art, herein provided are F(ab')$_2$, Fab, Fv, and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. Also described herein are single chain antibodies, domain antibodies and heavy chain antibodies.

In certain embodiments cell surface markers, adhesion molecules, or homing molecules of the circulating PVPC described herein are targeted by specific antibodies, or fragments thereof, to contact the PVPC with cytotoxic agents in order to kill the PVPC. Cytotoxic agents include cytotoxic radionuclides, chemical toxins and protein toxins. The cytotoxic radionuclide or radiotherapeutic isotope preferably is an alpha-emitting isotope such as $^{225}$Ac, $^{211}$At, $^{212}$Bi, $^{213}$Bi, $^{212}$Pb, $^{224}$Ra or $^{223}$Ra. Alternatively, the cytotoxic radionuclide may a beta-emitting isotope such as $^{186}$Rh, $^{188}$Rh, $^{177}$Lu, $^{90}$Y, $^{131}$I, $^{67}$Cu, $^{64}$Cu, $^{153}$Sm or $^{166}$Ho. Further, the cytotoxic radionuclide may emit Auger and low energy electrons and include the isotopes $^{125}$I, $^{123}$I or $^{77}$Br.

Suitable chemical toxins or chemotherapeutic agents may include members of the enediyne family of molecules, such as calicheamicin and esperamicin. Chemical toxins may also be taken from the group consisting of methotrexate, doxorubicin, melphalan, chlorambucil, ARA-C, vindesine, mitomycin C, cisplatin, etoposide, bleomycin and 5-fluorouracil. Toxins also include poisonous lectins, plant toxins such as ricin, abrin, modeccin, botulina and diphtheria toxins. Of course, combinations of the various toxins are also provided thereby accommodating variable cytotoxicity. Other chemotherapeutic agents are known to thos'e skilled in the art.

In certain embodiments cell adhesion molecules (CAMs) or homing molecules on the PVPC described herein may be targeted and blocked, as described herein, by downregulation of these molecules, for example, by siRNA molecules specific for certain CAMs, which may prevent migration and/or homing of the PVPC to the sites of vessel injury.

Inhibitor molecules that are short interfering nucleic acids (siNA), which include, short interfering RNA (siRNA), double-stranded RNA (dsRNA), micro-RNA (miRNA), and short hairpin RNA (shRNA) molecules are used to inhibit the expression of target genes. The siNAs described herein, for example siRNAs, typically regulate gene expression via target RNA transcript cleavage/degradation or translational repression of the target messenger RNA (mRNA). In one embodiment siRNAs are exogenously delivered to a cell. In a specific embodiment siRNA molecules are generated that specifically target CAMs specific for migration and/or homing of the PVPC to sites of vessel injury. A short interfering nucleic acid (siNA) described herein can be unmodified or chemically-modified. A siNA described herein can be chemically synthesized, expressed from a vector or enzymatically synthesized. Also provided herein are various chemically-modified synthetic short interfering nucleic acid (siNA) molecules capable of inhibiting gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. For example, in some cases, siRNAs are modified to alter potency, target affinity, the safety profile and/or the stability to render them resistant or partially resistant to intracellular degradation. Modifications, such as phosphorothioates, for example, can be made to siRNAs to increase resistance to nuclease degradation, binding affinity and/or uptake. In addition, hydrophobization and bioconjugation enhances siRNA delivery and targeting (De Paula et al., RNA. 13(4):431-56, 2007) and siRNAs with ribo-difluorotoluoyl nucleotides maintain gene silencing activity (Xia et al., ASC Chem. Biol. 1(3):176-83, (2006). siRNAs with amide-linked oligoribonucleosides have been generated that are more resistant to S1 nuclease degradation (Iwase R et al. 2006 Nucleic Acids Symp Ser 50: 175-176). In addition, modification of siRNA at the 2'-sugar position and phosphodiester linkage confers improved serum stability without loss of efficacy (Choung et al., Biochem. Biophys. Res. Commun. 342(3):919-26, 2006). In one study, 2'-deoxy-2'-fluoro-beta-D-arabinonucleic acid (FANA)-containing antisense oligonucleotides compared favourably to phosphorothioate oligonucleotides, 2'-O-methyl-RNA/DNA chimeric oligonucleotides and siRNAs in terms of suppression potency and resistance to degradation (Ferrari N et al. 2006 Ann NY Acad Sci 1082: 91-102).

In some embodiments an siNA is an shRNA molecule encoded by and expressed from a genomically integrated transgene or a plasmid-based expression vector. Thus, in some embodiments a molecule capable of inhibiting gene expression is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems. Examples of making and using such hairpin RNAs for gene silencing in mammalian cells are described in, for example, (Paddison et al., Genes Dev, 2002, 16:948-58; McCaffrey et al., Nature, 2002, 418:38-9; McManus et al., RNA 2002, 8:842-50; Yu et al., Proc Natl Acad Sci USA, 2002, 99:6047-52).

One embodiment herein contemplates the use of gene therapy to deliver one or more expression vectors, for example viral-based gene therapy, encoding one or more small interfering nucleic acids, capable of inhibiting expression of CAMs specific for migration and/or homing of the PVPC to sites of vessel injury. Methods for construction and delivery of expression vectors will be known to one of ordinary skill in the art.

In certain embodiments cell adhesion molecules (CAMs) or homing molecules on the PVPC described herein may be targeted and blocked, as described herein, by downregulation of these molecules, for example, by antisense molecules specific for certain CAMs, which may prevent migration and/or homing of the PVPC to the sites of vessel injury. Antisense nucleic acids include short oligonucleotides as well as longer nucleic acids. Preferably the antisense nucleic acids are complementary to and bind to portions of the coding sequence or 5' non-translated sequence of CAMs specific for migration and/or homing of the PVPC to sites of vessel injury, thereby inhibiting translation of functional polypeptides of these CAMs. Other antisense nucleic acids which reduce or block transcription of CAMs specific for migration and/or homing of the PVPC to sites of vessel injury are also useful.

Provided herein are antisense oligonucleotides that selectively bind to a nucleic acid molecule encoding a CAM specific for migration and/or homing of the PVPC to sites of vessel injury, to reduce the expression (transcription or translation) of that CAM. As used herein, the term "antisense oligonucleotide" describes an oligonucleotide that is an oligoribonucleotide, oligodeoxyribonucleotide, modified oligoribonucleotide, or modified oligodeoxyribonucleotide which hybridizes under physiological conditions to DNA comprising the CAM gene and, thereby, inhibits the transcription of that gene and/or the translation of that mRNA.

Those skilled in the art will recognize that the exact length of the antisense oligonucleotide and its degree of complementarity with its target will depend upon the specific target selected, including the sequence of the target and the particular bases which comprise that sequence. In certain embodiments, the antisense oligonucleotide is constructed and arranged so as to bind selectively with the target under physiological conditions, i.e., to hybridize substantially more to the target sequence than to any other sequence in the target cell under physiological conditions. Based upon the sequences of CAM nucleic acids, including allelic or homologous genomic and/or cDNA sequences, one of skill in the art can easily choose and synthesize any of a number of appropriate antisense molecules for use in accordance with the methods provided herein. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., Nature Biotechnol. 14:840-844, 1996). Most preferably, the antisense oligonucleotides comprise a complementary sequence of 20-30 bases.

Although oligonucleotides may be chosen which are antisense to any region of the gene or mRNA transcripts, in certain embodiments the antisense oligonucleotides correspond to N-terminal or 5' upstream sites such as translation initiation, transcription initiation or promoter sites. In addition, 3'-untranslated regions may be targeted.

Targeting to mRNA splicing sites has also been used in the art but may not be applicable if alternative mRNA splicing occurs. In addition, the antisense is targeted, preferably, to sites in which mRNA secondary structure is not expected (see, e.g., Sainio et al., Cell Mol. Neurobiol. 14(5):439-457, 1994) and at which proteins are not expected to bind. Finally, one of ordinary skill in the art may easily derive cDNA sequences and genomic DNA corresponding to CAMs from databases and published literature. Provided herein are antisense oligonucleotides which are complementary to the genomic DNA corresponding to nucleic acids encoding CAMs. Similarly, antisense to allelic or homologous cDNAs and genomic DNAs are enabled without undue experimentation.

In one set of embodiments, the antisense oligonucleotides described herein may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In certain embodiments, the antisense oligonucleotides described herein also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Synthetic internucleoside linkages are, for example, phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. Provided herein are in vitro uses of CAM antisense molecules as well as in vivo pharmaceutical preparations containing modified antisense molecules that are complementary to and hybridizable with, under physiological conditions, nucleic acids encoding CAMs, together with pharmaceutically acceptable carriers.

In another embodiment, the antisense nucleic acids described herein may be produced by expression in cells by expression vectors introduced therein. The choice and design of an appropriate vector is within the ability and discretion of one of ordinary skill in the art.

Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. According to this embodiment, cells, for example the PVPCs described herein, are genetically engineered by the introduction into the cells of heterologous DNA (RNA) encoding antisense CAM nucleic acid. The antisense CAM nucleic acid is placed under operable control of transcriptional elements to permit the expression of the antisense CAM nucleic acid in the PVPC host cell.

Systems useful for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr Virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710-4716, 1996). Additional vectors for delivery of antisense CAM nucleic acid will be known to one of ordinary skill in the art.

Various techniques may be employed for introducing antisense CAM nucleic acids into cells depending on whether the nucleic acids are introduced in vitro or in vivo in a host. Such techniques include transfection of nucleic acid-CaPO$_4$ precipitates, transfection of nucleic acids associated with DEAE, transfection or infection with viruses including the nucleic acid of interest, liposome mediated transfection, and the like. For certain uses, the nucleic acid is targeted to particular cells, such as the PVPCs described herein. In such instances, a vehicle used for delivering a nucleic acid described herein into a cell, such as the PVPC, (e.g., a retrovirus, adenovirus or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. Where liposomes are employed to deliver the nucleic acids described herein, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids and can also be used to deliver siRNAs or ribozymes and other agents described elsewhere herein.

In certain embodiments cell adhesion molecules (CAMs) or homing molecules on the PVPC described herein may be targeted and blocked, as described herein, by downregulation of these molecules, for example, by ribozymes specific for certain CAMs, which may prevent migration and/or homing of the PVPC to the sites of vessel injury.

A ribozyme is an RNA molecule that catalyzes a chemical reaction, such as the hydrolysis of one of its own phosphodiester bonds, or the hydrolysis of bonds in other RNAs. Trans-cleaving ribozymes can be artificially-produced to target specific RNAs, such as those of CAMs. Techniques to design and produce ribozymes are known in the art. For example, the ribozymes may be mutated by reverse transcription with reverse transcriptase into various cDNA and amplified with mutagenic PCR. The selection parameters in these experiments often differ. One approach for selecting a ribozyme involves using biotin tags, which are covalently linked to the substrate. If a ribozyme molecule possesses the desired activity, a streptavidin matrix can be used to recover the active ribozyme molecules. Certain ribozymes are already candidates for human therapy.

For example, a synthetic ribozyme that destroys the mRNA encoding a receptor of Vascular Endothelial Growth Factor (VEGF) is being readied for clinical trials. Modified hammerhead ribozymes are also being tested as therapeutic agents. Ribozymes described herein can be designed to specifically target CAMs on the PVPC described herein, therefore inhibiting PVPC migration and/or homing to sites of vessel injury. Methods to deliver ribozymes in vivo are known in the art and are also described elsewhere herein.

In certain embodiments, compounds or compositions of bioactive molecules such as small organic molecules, cytotoxic agents, antibodies and fragments thereof, peptides, cyclic peptides, nucleic acids, antisense nucleic acids, siRNAs, sphingolipid analogs, ribozymes, gene delivery vehicles, and/or cytokines that may be administered alone or in any combination to a subject in vivo or to PVPC cell cultures in vitro are provided.

The compositions described herein are administered to a subject in effective amounts. An "effective amount" is that amount of a composition that alone, or together with further doses, produces the desired response, e.g., killing of the PVPC described herein and/or the prevention of its migration and/or homing to sites of vessel injury, and/or a desired improvement in the condition or symptoms of the condition, e.g., for vascular diseases, such as atherosclerosis and pulmonary hypertension, this is a reduction in, or prevention of, structural defects or changes of the blood vessels, such as a reduction in inflammation and/or tissue damage and/or build-ups that block normal blood flow. This can be monitored by routine methods known to one of ordinary skill in the art, such as for example CT (computerized tomography) scan, Magnetic Resonance Angiography, Ankle Brachial Index, Ultrasound Doppler Test, and other methods described herein. The amount effective can be the amount of a single agent that produces a desired result or can be the amount of two or more agents in combination. Such amounts can be determined with no more than routine experimentation.

It is believed that doses ranging from 1 nanogram/kilogram to 100 milligrams/kilogram, depending upon the mode of administration, will be effective, but any other dose may also be feasible. The absolute amounts administered in vivo may depend, of course, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. In certain embodiments, a maximum dose of the individual components or combinations thereof is used, that is, the highest safe dose according to sound medical judgment. It will be understood by those of ordinary skill in the art, however, that a patient may insist upon a lower dose or tolerable dose for medical reasons, psychological reasons or for virtually any other reasons. In the event that a response in a subject is insufficient at the initial doses applied, higher doses (or effectively higher doses by a different, more localized delivery route) may be employed to the extent that patient tolerance permits.

When administered in vivo, the compositions described herein can be administered in pharmaceutically acceptable preparations. Such preparations may routinely contain pharmaceutically acceptable concentrations of salt, buffering agents, preservatives, compatible carriers, supplementary immune potentiating or immune suppressive agents such as adjuvants and cytokines and optionally other therapeutic agents.

The compositions used in the foregoing methods preferably are sterile and contain an effective amount of one or more agents for producing the desired response in a unit of weight or volume suitable for addition to a cell culture in vitro or administration to a subject in vivo. As used herein, a subject is a human or non-human animal, including non-human primates, mice, rats, cows, pigs, horses, sheep, goats, dogs, cats, etc. Preferably the subject is a human.

When administered to a subject, the pharmaceutical preparations described herein are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may also conveniently be used to prepare pharmaceutically-acceptable salts thereof. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, naphthalene-2-sulphonic, and benzene sulphonic, and the like. Also, pharmaceutically-acceptable salts can be prepared as alkaline metal or alkaline earth salts, such as sodium, potassium or calcium salts.

The pharmaceutical compositions may contain suitable buffering agents, including: acetic acid in a salt; citric acid in a salt; boric acid in a salt; and phosphoric acid in a salt. Suitable buffering agents include: acetic acid and a salt (1-2% W/V); citric acid and a salt (1-3% W/V); boric acid and a salt (0.5-2.5% WN); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V). The pharmaceutical compositions also may contain, optionally, suitable preservatives, such as: benzalkonium chloride; chlorobutanol; parabens and thimerosal.

Any compound or composition described herein may be combined, if desired, with a pharmaceutically-acceptable carrier. The term "pharmaceutically-acceptable carrier" as used herein means one or more compatible solid or liquid fillers, diluents or encapsulating substances which are suitable for administration, for example, into a human. The term "carrier" denotes an organic or inorganic ingredient, natural or synthetic, with which the active ingredient is combined to facilitate the application. The components of the pharmaceutical compositions also are capable of being comingled with the molecules described herein, and with each other, in a manner such that there is no interaction which would substantially impair the desired pharmaceutical efficacy.

The pharmaceutical compositions may conveniently be presented in unit dosage form and may be prepared by any of the methods well-known in the art of pharmacy. Methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product. Among the acceptable vehicles and solvents that may be employed are water, Ringer's solution, and isotonic sodium chloride solution, but are not so limited. In addition, sterile, fixed oils are conventionally employed as a solvent or suspending medium. For this purpose any bland fixed oil may be employed including synthetic mono- or di-glycerides. Carrier formulation suitable for oral, subcutaneous, intravenous, intramuscular, etc. administrations can be found in *Remington's Pharmaceutical Sciences*, Mack Publishing Co., Easton, Pa.

The therapeutical compounds and compositions provided herein can be administered in vivo by any conventional route, including injection or by gradual infusion over time. The administration may, for example, be oral, intravenous, intraperitoneal, intramuscular, intracavity, subcutaneous, intrasternal, and transdermal. Other modes of administration include mucosal, rectal, vaginal, sublingual, intranasal, intratracheal, inhalation, and ocular. For oral administration, the compounds can be formulated readily by combining the active compound(s) with pharmaceutically acceptable carriers well known in the art. Such carriers enable the compounds described herein to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for uses described herein may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The compositions may conveniently be presented in unit dosage form and may be prepared by any of the methods well known in the art of pharmacy.

Other delivery systems can include time-release, delayed release or sustained release delivery systems. Such systems can avoid repeated administrations of the compounds described herein, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775 (Kent); 4,667,014 (Nestor et al.); and 4,748,034 and 5,239,660 (Leonard) and (b) diffusional systems in which an active component permeates at a controlled rate through a polymer, found in U.S. Pat. Nos. 3,832,253 (Higuchi et al.) and 3,854,480 (Zaffaroni). In addition, a pump-based hardware delivery system can be used, some of which are adapted for implantation.

Controlled release can also be achieved with appropriate excipient materials that are biocompatible and biodegradable. These polymeric materials which effect slow release may be any suitable polymeric material for generating particles, including, but not limited to, nonbioerodable/non-biodegradable and bioerodable/biodegradable polymers.

Such polymers have been described in great detail in the literature and are well known in the art. They include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxyethyl cellulose, cellulose triacetate, cellulose sulfate sodium salt, poly(methyl methacrylate), poly (ethylmethacrylate), poly(butylmethacrylate), poly(isobutylmethacrylate), poly(hexlmethacrylate), poly (isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly (ethylene oxide), poly(ethylene terephthalate), poly(vinyl alcohols), poly(vinyl acetate, poly vinyl chloride polystyrene, polyvinylpryrrolidone, hyaluronic acid, and chondroitin sulfate. Examples of non-biodegradable polymers include, but are not limited to, ethylene vinyl acetate, poly(meth) acrylic acid, polyamides, copolymers and mixtures thereof. Examples of biodegradable polymers include, but are not limited to, synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. Polymers are, for example, polyesters, polyanhydrides, polystyrenes and blends thereof.

"Vascular disease" as used herein is a disease of blood vessels, that includes peripheral vascular disease, pulmonary vascular disease, coronary heart disease, collagen vascular disease, occlusive vascular disease and others.

Peripheral vascular disease (PAD) is a disorder caused by the blockage of blood vessels to the brain and extremities, e.g., as a result from atherosclerosis ('hardening of the arteries") leading to stenosis (blockage) and blood clots, and causes either acute or chronic ischemia. Atherosclerosis is a disease in which plaques containing fatty substances, such as cholesterol, are formed within the inner layers of the arteries (hardening of an artery specifically due to an atheromatous plaque). It is a progressive condition occurring over decades in human subjects, and primarily affects the arteries of the heart, brain and extremities. Its complications include heart attack, stroke or peripheral arterial occlusion.

Ischemia is an oxygen deficiency in organ tissues that may be due to constriction of obstruction in vessels supplying blood to a particular body part, which can lead to a heart attack (acute myocardial infarction). Myocardial infarction is necrosis (tissue death) of a region of the myocardium caused by an interruption in the supply of blood to the heart, usually as a result of occlusion of a coronary artery. An occlusive thrombosis of a coronary artery is precipitated by fissure of an atheromatous plaque in the vessel wall. Ischemic heart disease (coronary heart disease) is caused by reduced blood flow to the heart. Vessel constriction can also lead to other symptoms, such as renovascular hypertension (high blood pressure) caused by narrowing of the arteries that carry blood to the kidneys, or pulmonary hypertension (PH), which is an increase in blood pressure in the pulmonary artery, pulmonary vein, or pulmonary capillaries (lung vasculature) leading to shortness of breath, dizziness, and fainting in a subject.

The present invention is further illustrated by the following Examples, which in no way should be construed as further limiting. The entire contents of all of the references (including literature references, issued patents, and published patent applications) cited throughout this application are hereby expressly incorporated by reference.

EXAMPLES

Balloon Injury of Carotid Artery

Arterial trauma and endothelial cell denudation was induced in the left common carotid artery of 10 to 15 week old male Fisher rats. The rats were anesthetized using combination of ketamine (45 mg/kg) and xylazine (5 mg/kg) and by aseptic surgical technique the left common carotid artery was exteriorized through a ventral midline neck incision. A 2F Fogarty arterial embolectomy catheter (Edwards Lifesciences, S. A., Ch. duGlapin, 61162, Saint-Prex, Switzerland, Horw, Switzerland) was inserted into the lumen of the artery in a caudal direction via an arteriotomy. The catheter was advanced for a distance of 1 cm, and the balloon distended using 0.12 ml of physiological saline and the stop cork closed to retain this pressure on the distended balloon, so as to generate slight arterial wall resistance while the catheter is slowly withdrawn and then pushed forward three times after which the catheter was removed from the arterial lumen. The lumen was flushed with 1 ml heparin solution (50 IU/ml) and the arteriotomy was closed using 10-0 silk suture, and the surgical wound closed using 4-0 Vicryl sutures. A separate group of rats were injected with PVPC transduced with lenti-GFP vector ($5 \times 10^6$ PVPC each rat) into the site of carotid artery injury. The SHAM rats underwent similar surgical process except for the vascular injury ±PBS.

Haematoxylin and Eosin Staining

Three weeks post carotid artery injury the rats were euthanized by overdose of pentobarbital (100 mg/kg i.p.) and the carotid artery was collected and embedded in OCT after being perfusion fixed using chilled heparinised-PBS (50 U/ml) and 4% paraformaldehyde. 6 μM thick sections from carotid artery were cut and stained with haematoxylin and eosin for histological analysis. The images were acquired using Nikon (E 80 I upright) microscope and quantified using the NIH ImageJ software.

Immunofluorescence: Carotid Arterial Sections

6 μM thick sections from carotid artery were cut and stained for GFP (Abcam 1:500, rabbit polyclonal) and a smooth muscle actin (Dako 1:250, clone 1A4). Goat anti rabbit-Alexa Fluor 488 and Goat anti-mouse Alexa Fluor 546 were used as secondary antibodies and DAPI was used for nuclear staining. Images were acquired using confocal laser detection (Nikon eC1 plus, TE2000E).

Isolation of PVPC from Carotid Artery

Three weeks post vascular injury ±PVPC or PBS; the rats were euthanized by overdose of pentobarbital (100 mg/kg i.p.) and the carotid artery perfused with heparinised-PBS (50 U/ml), isolated and cleared of perivascular fat and connective tissue and cut into 5 mm rings. The carotid rings were further washed with sterile PBS for 3 times and incubated in 0.1% collagenase solution at 37° C. for 30 mins following which the rings were transferred into $EGM_2$ media in a 6 well plate and observed every day for the presence of GFP positive PVPCs.

PVPC Outgrowth

Bone marrow derived PVPC were isolated from primary cultures of rat whole bone marrow. Femars and tibias were flushed with RPMI supplemented with 100 U penicillin/streptomyocin. Cells were passed through a 40 um strainer and collected by centrification at 300×g for 10 mins at 4° C. RBCs lysed with 5 mL ACK buffer for 5 mins at room temperature and washed in 45 mL PBS. Cells were collected by centrification at 600×g for 5 min. BMCs were washed three times with 4 mL MCBD 131 supplemented with 100 U hydrocortisone acetate, 100 U penicillin/streptomyocin, 20 ng/mL ampotercin B, 10 ng/mL VEGF and 0.5 mg/mL Dibutylyl cAMP. Cells were resuspended in EGM-2 at $5 \times 10^6$ cells/mL and plated on collagen type I coated plates. Unattached cells were removed after five days and media was changed with fresh 37° C. EGM-2 every three days after. PVPC colonies were identified as strong phase contrast cells growing on the edge to other BMC colonies. Colonies were removed from primary BMC outgrowth by gentle washing with PBS. PVPC colonies were transferred to a fresh 6-well plate and expanded to confluency.

Immunoflourescent Staining

In vitro cell cultures were fixed in 4% paraformaldehyde/PBS for 20 minutes at 4° C. and washed twice with PBS. Cells were blocked and permeablized with 0.1% Triton-X 100/PBS and 10% normal serum, stained with primary antibodies Oct4 (Abcam 1:500), Isl-1 (DSHB 1:1000) overnight at 4° C., washed then visualized with secondary anti-mouse Alexa Flour 488 (Invitrogen 1:1000). Images were acquired using confocal laser detection (Nikon eC 1 plus, TE2000E).

Lentiviral Integration Southern Blot

Isolated PVPCs were transduced with 1 MOI of FIV-GFP. Cells were cultured to confluency before isolation of genomic DNA by DNeasy Isolation Kit (Qiagen). Genomic DNA was digested with restriction endonuclease overnight and fragments separated by electrophoresis on a 1% PAGE gel. Fragments were probed using digoxygenin labeled oligo to GFP region of the vector.

Clonegenic Outgrowth Assay

Transduced PVPC were diluted to 0.3 cells/mL in EGM-2 and 200 ul were plated into each well of 96 well plate. Wells with single cells were identified, grown to confluency and transferred to 6 well plate. This was repeated for secondary and tertiary clones. Genomic DNA was isolated from each successive cycle and integration was identified by southern blot.

Telomerase Assay

TeloTAGGG Telomerase ELISA PCR kit (Roche Scientific) used to quantitate telomerase activity. Briefly, $2\times10^5$ PVPC or rSMC were harvested and washed twice in PBS. Cells were incubated with Lysis Reagent for 30 minutes, cleared by centrifugation at 16000×g for 20 minutes. Extract was used for Telomere Repeat Amplification PCR with 30 min primer elongation and 30 cycles of amplification as described. PAGE gel resolution and ELISA quantification were carried out using the product.

Matrigel Tube Forming Assay

Matrigel (Becton Dickinson; San Jose, Calif.) was thawed at 4° C. overnight. Wells in a 24-well plate were coated with 250 µl of liquid Matrigel per well. The coated wells were then incubated at 37° C. for 30 min. PVPC and EPCs were mixed, seeded into each well and incubated for 24 h. During this period, the morphologic changes of the cells were observed and recorded under a microscope.

HR-SMTHB Lentiviral Transduction and Smoothelin Promoter Activity

The 3561 by human Smoothelin-B promoter (−3372/+120) was cloned from human genomic DNA and inserted in the EcoRI-BamHI sites of theHR-CSGW construct (kindly provided by Adrian Thrasher, Institute of Child Health, London, United Kingdom). Generation of lentiviral vectors was accomplished by a three-plasmid calcium phosphate transfection procedure. Briefly, 293T cells were transfected with the transfer plasmid vector together with two expression vectors; pCMV-ΔR8.91 encoding the packaging proteins Gag-Pol, Rev, Tat, and pMD.G encoding G protein of the vesicular stomatitis virus (VSV). PVPC were transduced with 10 MOI HR-SMTHB overnight in EGM-2. Seven days after transduction, PVPC/HR-SMTHB were plated.

FACS

Cells were lifted using Versene and washed twice with PBS. For extracellular markers, cells were washed with 0.5% PBSA and stained for 1 hour with primary antibodies against al integrin (SCBT 1:250) β1 integrin (SCBT 1:250), β2 integrin (SCBT 1:200) β3 integrin (SCBT 1:200) α2β1 integrin (SCBT 1:200) α5β1 integrin (SCBT 1:200) αvβ3 integrin (SCBT 1:200) αvβ5 integrin (1:200) CD133 (Miltenyi 1:500) CD34 (SCBT 1:100) CD45 (SCBT 1:100). For intracellular markers, cells were fixed for 30 minutes in 2% paraformaldehyde at 4 C and permeabilized with 0.2% Tween-20/PBS at 37 C for 15 minutes or with two washes with 0.5% saponin on ice. Cells were stained with primary antibodies against eNOS (BD 1:1000) Flk-1 (SCBT 1:100) αSMA (Dako 1:250) Myosin HC (Dako 1:20) Calponin (Dako 1:250) smoothelin-B (SCBT 1:200). Live cells were gated on forward and side scatters using BD FACSCaliber (BD) and analysed using BD FACSComp software.

Monocrotaline Induced Pulmonary Hypertension

Female Fischer 334 rats were injected with 60 mg/kg monocroataline by IP. Monocrotaline was made up as following; 400 mg monocrotaline-hydrocholride (Oak Ridge Labs) was dissolved in 6 mL 0.9% saline, 0.45 mL 5N HCL then 0.12 mL 10N NaOH and adjusted to pH 7.4. Twenty four days after injection, rats were anesthetized with 45 mg/kg ketamine and 5 mg/kg xylazine, left carotid exposed, and umbilical vein catheter is passed into the right ventricle. Invasive blood pressure is measured with a (Phillips) and traced for 30 seconds to measure average peak and mean right systolic ventricular pressure (RSVP). To prevent low RSVP due to dehydration, after initial measurement, 1 mL of 0.9% saline is administered to the RV. Blood pressure was allowed to stabilize for 5 minutes before a second average peak and mean RSVP is taken. This is repeated until 2 measurements are within 5% of each other.

mRNA Isolation from Blood 8 ml of human blood are used to yield approximately 30 µg of RNA. All of the tubes and solutions in this protocol must be RNAse-free. [Adapted from Genomic Medicine Biorepository]

1) Transfer contents of tube into a 50 ml polypropylene conical centrifuge tube.
2) Bring volume to 50 ml with 1XRBC Lysis Buffer.
3) Incubate at room temperature for 10 to 15 minutes.
4) Pellet cells at 600×g for 10 minutes in a 4° C. centrifuge.
5) Decant supernatant.
6) Gently resuspend pellet in 1 ml of RBC Lysis Buffer and transfer to a 1.5 ml microcentrifuge tube. —Incubate for 2 to 5 minutes.
7) Pellet cells in a microfuge at 3000 rpm for 2 minutes (room temperature).
8) Aspirate the supernatant.
9) If resulting pellet is still red, repeat the RBC lysis (steps 6, 7, and 8).
10) Resuspend pellet in 1 ml of sterile PBS.
11) Pellet cells as in step 7.
12) Aspirate the supernatant.
13) Add 800 µl of TRIzol/RNAstat60 solution and resuspend the cells.
14) Add 0.2 ml of Chloroform ($CHCl_3$) and vortex for 15 seconds.
15) Incubate on ice for 5 to 10 minutes.
16) Centrifuge samples in a microfuge at 14,000 rpm for 15 minutes at 4° C.
17) Remove the upper phase and transfer to a clean microcentrifuge tube to which an equivalent volume of ice-cold isopropanol is added. Immediately vortex and place on ice for 15 minutes.
18) Centrifuge samples in a microfuge at 14,000 rpm for 15 minutes at 4° C.
19) Carefully decant the supernatant, and rinse the pellet with 0.5 ml of ice-cold 75% ethanol.

20) Centrifuge samples in a microfuge at 7500 rpm for 8 minutes at 4° C.
21) Decant the supernatant.
22) Quick-spin the samples (14,000 rpm, 30 seconds, 4° C.)
23) Remove all of the remaining liquid in the bottom of the tube.
24) Allow pellet to dry for 5 to 10 minutes to remove any remaining ethanol.
25) Dissolve the RNA pellet in 30 to 50 μl of RNAse-free H2O to each sample.
26) Quantitate ($OD_{260}$) and use RNA as needed.
10×RBC Lysis Buffer (89.9 g NH4Cl, 10.0 g KHCO3, 2.0 ml 0.5 M EDTA, dissolve in 1 liter ddH2O and adjust pH to 7.3). TRIzol Reagent (Invitrogen Life Technologies: Cat No. 15596018) or RNA STAT-60 Reagent (Tel-Test: Cat No. CS-111).

Cardiomyocyte Differentiation Method.

PVPC were initially transduced with lentivirus encoding GFP which allowed distinction of PVPC from co-cultured cells. To examine cardiomyocyte differentiation, GFP labeled PVPC were co-cultured in the presence of freshly isolated beating rat neonatal cardiomyocytes. Cells were grown in cardiomyocyte favorable differentiation media as previously described. Cultures were extended over 5-7 days and cardiomyocyte differentiation was assessed using immunofluorescence for cardiac specific markers and functional assessment in terms of contractility.

Endothelial Cell Differentiation Method

PVPC were grown on collagen type 1 or fibronectin in the presence of EGM-2 media with VEGF added (50 ng/ml) endothelial differentiation media (EDM). Endothelial markers such as eNOS, CD31 and VECadherin were assessed after 1, 2 and three weeks of EDM culture. In separate experiments PVPC were grown on Matrigel in the presence of EDM or in the presence or absence of endothelial progenitor cells in the case of GFP labeled PVPC. The capacity of VPC to form tubes in Matrigel was assessed.

Smooth Muscle Cell (SMC) Differentiation Method

PVPC were grown on type 1 collagen in the presence of smooth muscle differentiation media (SmDM) (SMGM-2+ PDGF 100 ng/ml or TGFbeta1 100 ng/ml). Cells were maintained in SmDM for 1, 2 and 3 weeks and smooth muscle markers assessed in addition to smoothelin promter activity (indicative of smooth muscle differentiation). In separate experiments PVPC were exposed to thrombin which we have shown augments SMC differentiation. PVPC were assessed for myocardin following exposure to SMC differentiation conditions. Cells were also subsequently stimulated with KCL or angiotensin II and calcium signaling and cell contraction were functionally assessed respectively. These effects were also evaluated in the presence or absence of a calcium antagonist Nifedipine.

Example 1

PVPC were isolated from bypass filters of human patients with coronary disease undergoing coronary artery bypass graft (CABG) and cells were isolated from filters of matched patients undergoing valve surgery without coronary artery disease. The isolated cells were suspended in culture medium and plated. The cells were incubated for different times and colonies were counted using a microscope. FIG. 1A shows a photograph of colonies forming from PVPC isolated from bypass filters of patients with coronary disease. FIG. 1B shows a comparison of PVPC outgrow (measure as VPC: CFU=PVPC colony forming units) of PVPC isolated from bypass filters of human patients with coronary disease and cells isolated from filters of matched patients undergoing valve surgery without coronary artery disease (n=6 patients). FIG. 1B shows that no colonies could be detected (ND Not detectable) from cells isolated from filters of matched patients undergoing valve surgery without coronary artery disease. This data show that PVPC are not found in peripheral blood from patients without coronary artery disease.

Example 2

Figure 2:
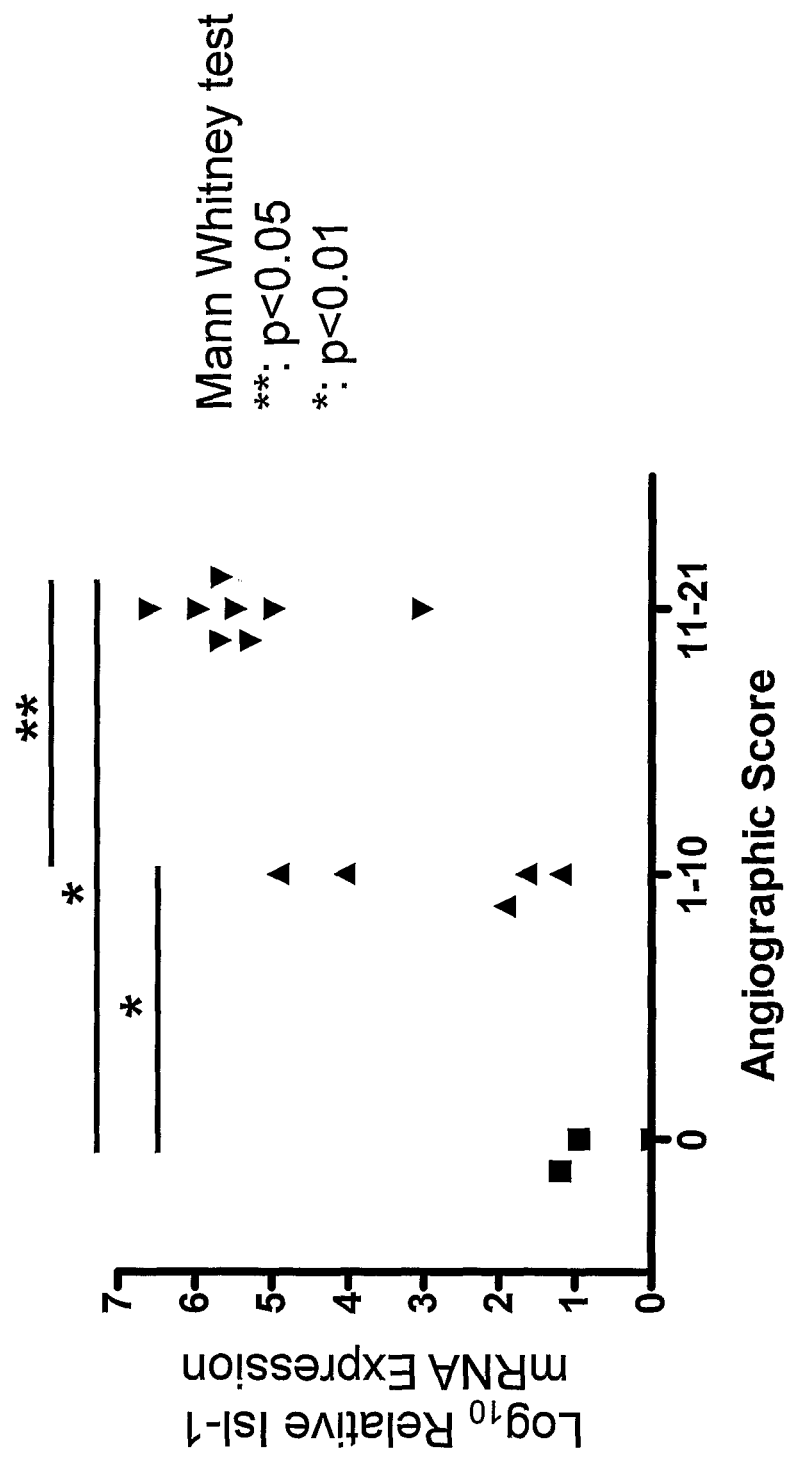
FIG. 2 depicts Isl-1 mRNA expression in peripheral blood mononuclear cells isolated from patients with coronary artery disease (CAD—1-21 score) and normal control subjects (0 score) without disease at angiography.

Peripheral blood mononuclear cells (PBMNC) were isolated from human patients with coronary artery disease (CAD—1-21 score) and normal control subjects (0 score) without disease at angiography. The CAD patients received an angiographic score according to disease burden. RNA was isolated and qRT-PCR for Isl-1 was performed on PBMNC RNA isolates. FIG. 2 shows a correlation between Isl-1 mRNA expression and CAD score, associated with disease burden. Isl-1 mRNA expression in PBMNC from patients with high CAD scores (11-21) was 5-6 logs higher than that of control subjects (0 score). This data show that Isl-1 mRNA expression in PBMNC is correlated with coronary artery disease burden, as measured by CAD-score.

Example 3

Figure 3:
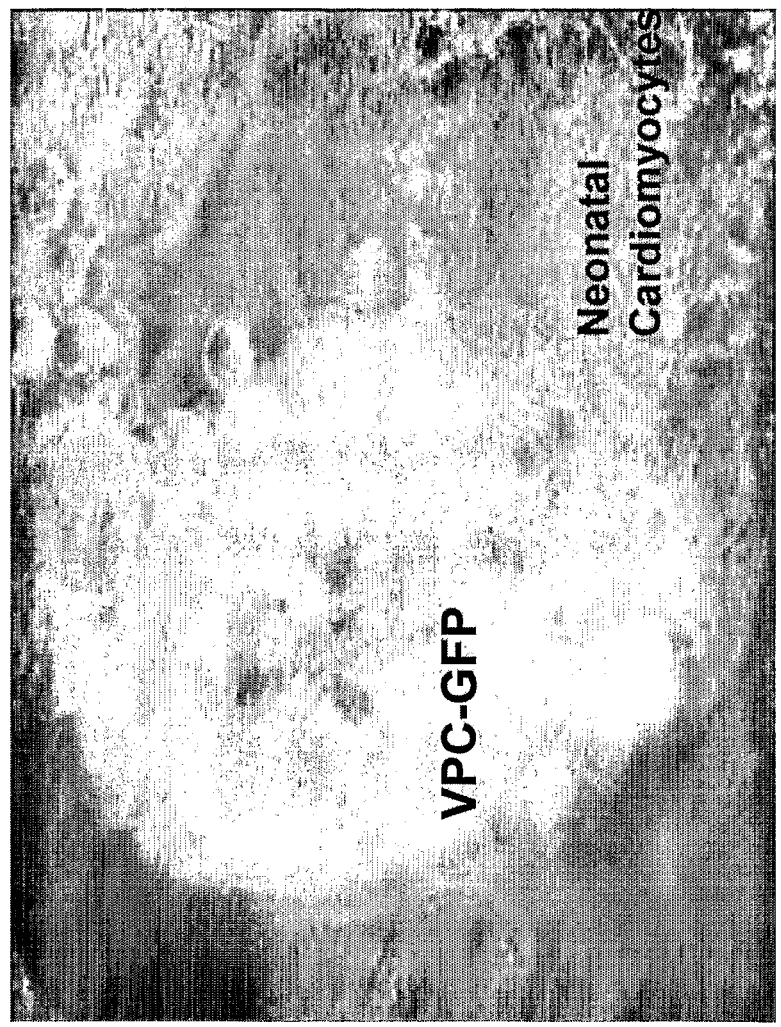
FIG. 3 depicts a PVPC differentiation assay in which PVPC were grown on a layer of beating rat neonatal cardiomyocytes.

PVPC were isolated from human patients with coronary disease and were added and grown on a layer of beating rat neonatal cardiomyocytes in a differentiation assay. FIG. 3 shows that PVPC failed to differentiate along a cardiomyocyte lineage (n=4 experiments). This data show that PVPC cannot contribute to the cardiomyocyte lineage.

Example 4 rVPC were isolated from rat bone marrow and the ability to form colonies in vitro and stem-like characteristics were analyzed.

Figure 4:
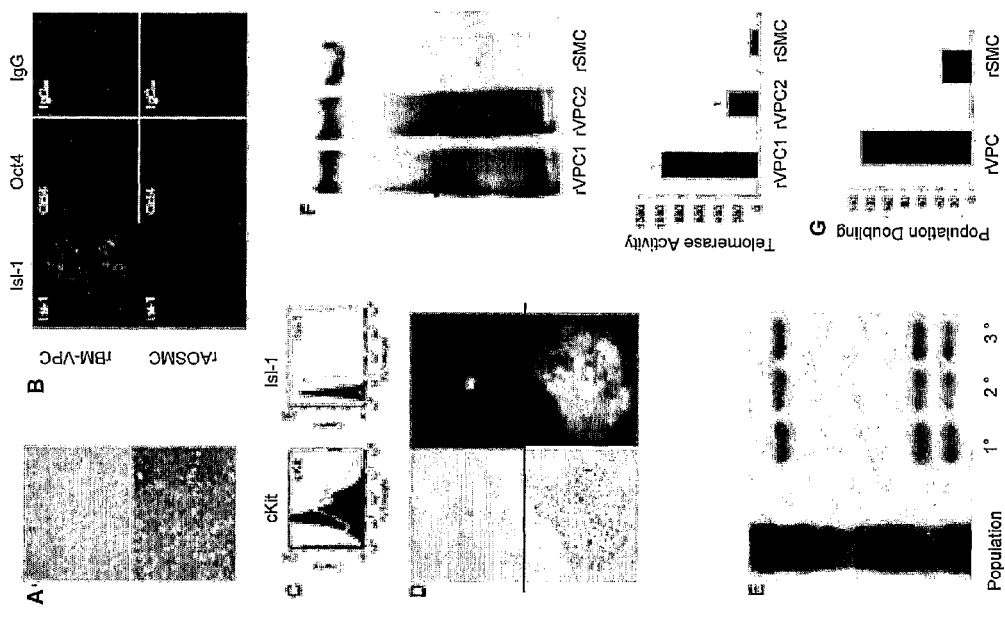
FIG. 4 depicts results showing colony formation and stem-like characteristics of rat VPC grown from rat bone marrow. 4A depicts phase contrast images of rat VPC colonies at initial colony outgrowth stage and after passage. 4B depicts immunofluorescence staining of rVPC for ISL-1 and Oct-4. 4C depicts a FACS profile of rVPC labeled cKit and ISL-1. 4D depicts phase contrast and immunofluorescence pictures of clonal expansion of single cell rVPC (with integrated lentiviral vector encoding GFP). 4E depicts a Southern blot showing triple integration sites of lentivirus following clonal expansion. 4F depicts Western blot showing high telomerase expression/activity in late passage rat VPC and a quantitation of telomerase activity (bar graph). 4G depicts a bar graph showing extended self renewal capacity of rVPC.

FIG. 4A shows a phase contrast images of rat VPC (rVPC) colonies at initial colony outgrowth stage (upper panel) and after passage (lower panel). FIG. 4B shows immunofluorescence staining of rVPC (rBM-VPC, upper panel) for ISL-1 and Oct-4 and absence of IgG control. Rat smooth muscle cells (rAOSMC, lower panel) serve as controls and ISL-1 and Oct-4 were not detected. A FACS profile shows rVPC labeled cKit and ISL-1 (FIG. 4C). Single cell rVPC (upper panel) were clonally expanded (lower panel) following integration of a lentiviral vector encoding GFP (FIG. 4D, left panel: phase contrast; right panel: GFP). The lentivirus vector was integrated and the Southern blot of FIG. 4E shows triple integration sites of the lentivirus following clonal expansion of transduced GFP-positive rVPC during, primary, secondary and tertiary passage. Stem-like characteristics of rVPC were analyzed. FIG. 4F shows the results obtained for telomerase activity, which was measured by PAGE and quantified (bar graph). High telomerase expression/activity was measured in late passage rat VPC and telomerase activity was absent in similarly passaged control smooth muscle cells (rSMC). Extended self-renewal capacity of rVPC growing beyond Hayflick limit to >120 population doublings (PD) was observed (FIG. 4G). As controls, smooth muscle cells were measured. rSMC become senescent before the Hayflick limit ~70 PD (FIG. 4G).

Example 5

Figure 5:
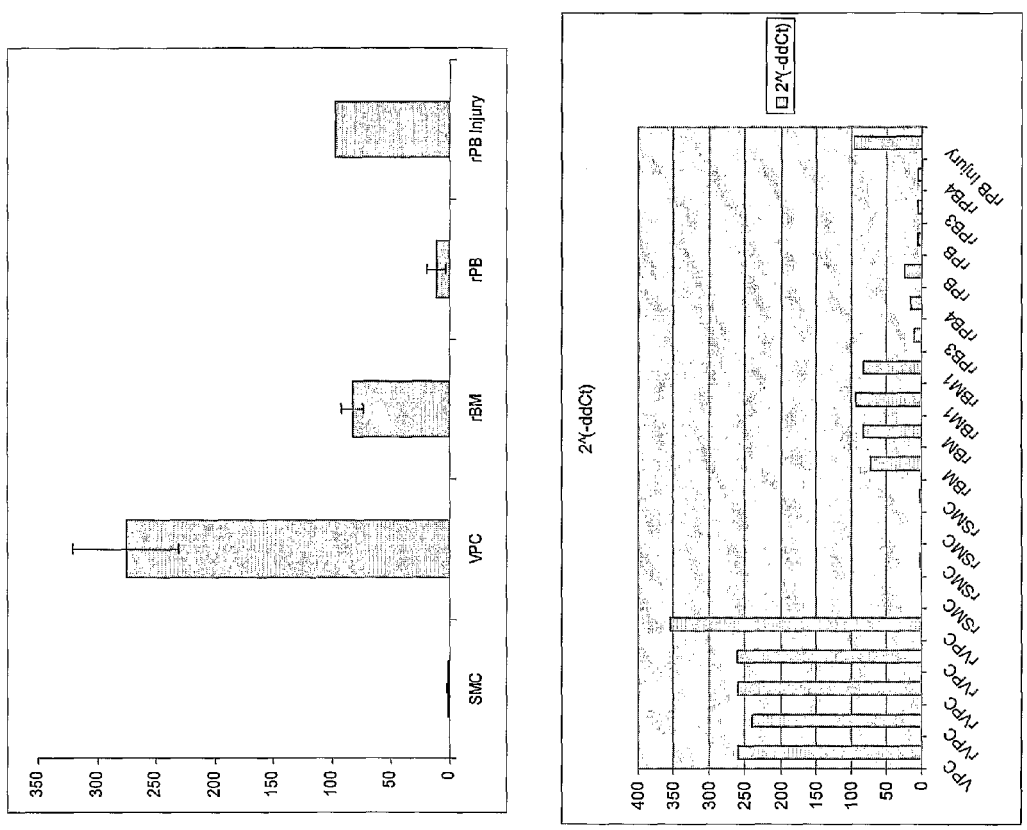
FIG. 5 depicts results showing marked elevation in mRNA for ISL-1 in rat VPC, in bone marrow and blood after angioplasty injury. Upper panel shows quantitative RT-PCR histograms for ISL-1 mRNA in VPC and in bone marrow (BM) and in peripheral blood (rPB) after arterial injury with an angioplasty balloon, normal rPB, and smooth muscle cells (SMC). Lower panel shows individual values for each group.

ISL-1 mRNA expression was measure by qRT-PCR in various samples. Marked elevation in mRNA for ISL 1 in rat VPC, in bone marrow and blood after angioplasty injury was detected. FIG. 5 (upper panel) shows quantitative RT-PCR histograms for ISL-1 with elevation in ISL1 mRNA in rVPC and in bone marrow (rBM) and in peripheral blood (rPB) after arterial injury with an angioplasty balloon (rPB Injury). ISL-1 mRNA could not be detected in normal rPB or smooth muscle cells (SMC) or a number of other blood cells such as monocytes or lymphocytes. Lower panel shows individual values for each group.

Figure 6:
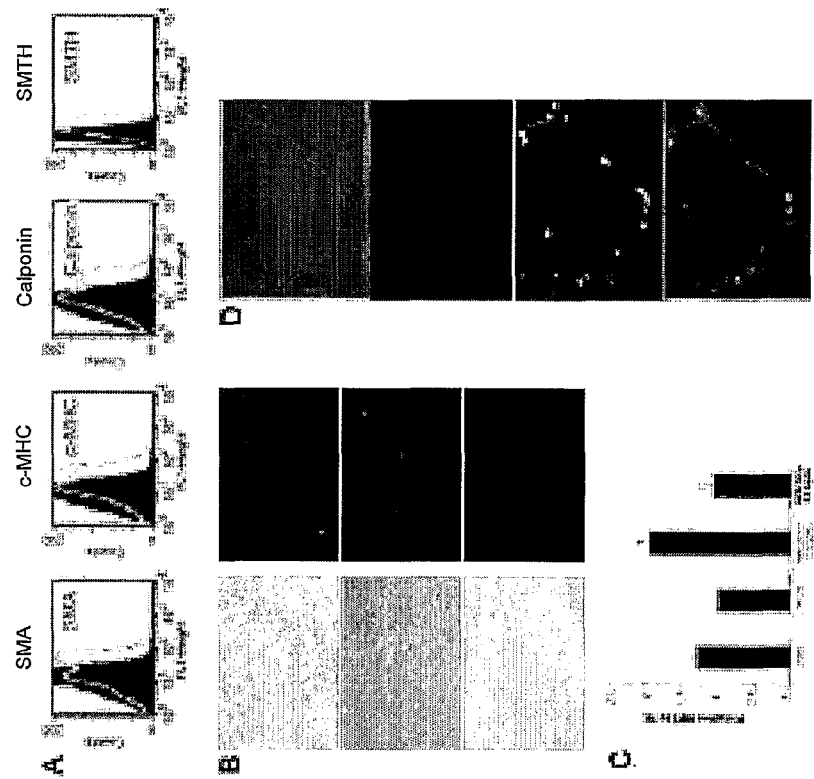
FIG. 6 depicts results showing certain characteristics of rVPC. 6A depicts a FACS profile of VPC showing expression of smooth muscle actin (SMA), myosin heavy chain (MHC) and calponin and smoothelin (SMTH) in cultured cells. 6B depicts phase contrast and immonufluorescence images showing smoothelin promoter activity in VPC transduced with a lentivirus encoding the smoothelin promoter driving GFP (upper panel) compared to smooth muscle cells (rAOSMC, middle panel) and endothelial cells (lower panel). 6C depicts a graph showing histograms for relative promoter activity under control of PDGF BB but not TGF beta. 6D. depicts images showing capacity of rVPC to form pericyte-like structures around endothelial progenitor cell (EPC) tubes. Merged image (bottom panel) shows rVPC at the edge of EPC within the Matrigel tube.

Example 6 rVPC show certain characteristics of smooth muscle cell differentiation. FIG. 6A shows the FACS profile of rVPC showing expression of smooth muscle actin (SMA), myosin heavy chain (MHC), calponin, and smoothelin (SMTH) in cultured cells. rVPC were transduced with a lentivirus encoding the smoothelin promoter driving GFP. FIG. 6B shows smoothelin promoter activity in VPC (upper panel). Similar promoter activity is seen in smooth muscle cells (rAOSMC, middle panel) but not endothelial cells (lower panel). The bar graph of FIG. 6C shows histograms for relative promoter activity under control of PDGF BB but not TGF beta. VPC were functionally assessed. VPC have the capacity to form pericyte-like structures (indicative of SMC-like differentiation) around endothelial progenitor cell (EPC) tubes (FIG. 6D). Merged image shows VPC at the edge of EPC within the Matrigel tube. VPC do not form tubes alone, in contrast to EPC.

Example 7

Figure 7:
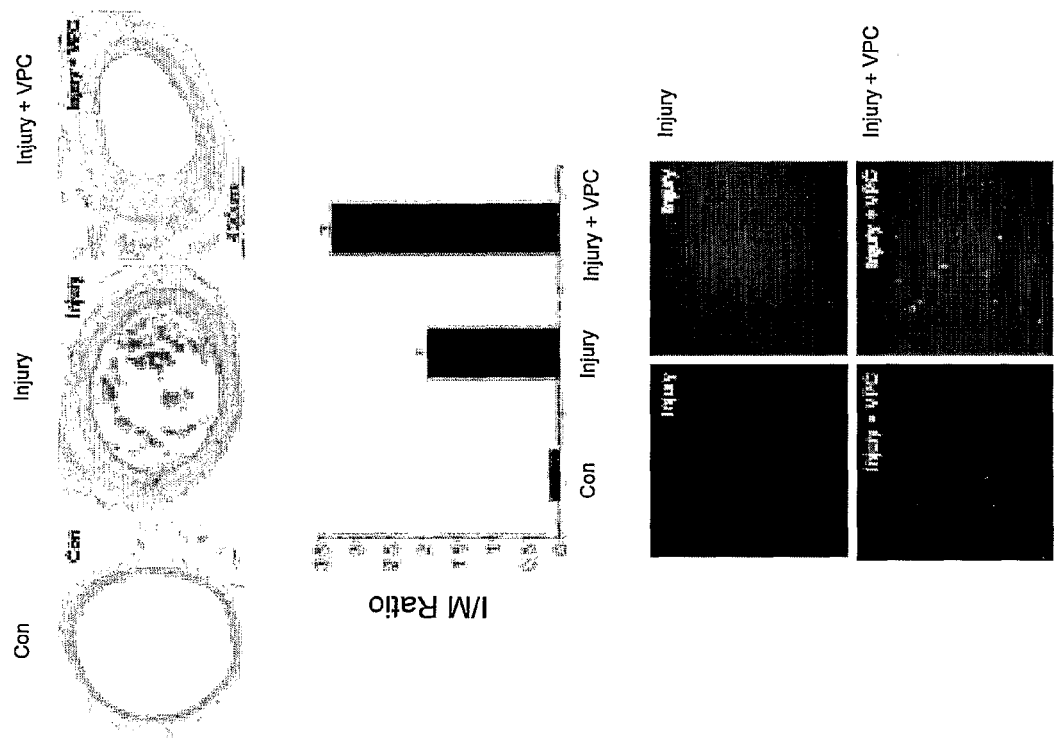
FIG. 7 depicts results showing exogenously administered VPC contribute to neointimal growth post angioplasty in rat in vivo. Top and middle panels show neointimal growth indicated by intima/media ratio calculation. Top panel shows representative H&E stained sections from each treatment group (con=control, injury=balloon denudation, and injury+VPC+balloon injured animals with VPC administered into vessel). Lower panel shows ability to re-isolate GFP labeled VPC from neointimal plaque of VPC treated animals.

The contribution of exogenously administered VPC to neointimal growth post angioplasty in rat was assessed in vivo. FIG. 7 top and middle panels show neointimal growth indicated by intimalmedia ratio (I/M ratio, middle panel) calculation is increased following balloon denudation of rat carotid injury and VPC increase this growth even further. Top panel (H&E stain) shows representative sections from each treatment group (con=control, injury=balloon denudation, and injury+VPC+balloon injured animals with VPC administered into vessel). Lower panel shows ability to re-isolate GFP labeled VPC from neointimal plaque of VPC treated animals.

Example 8

Figure 8:
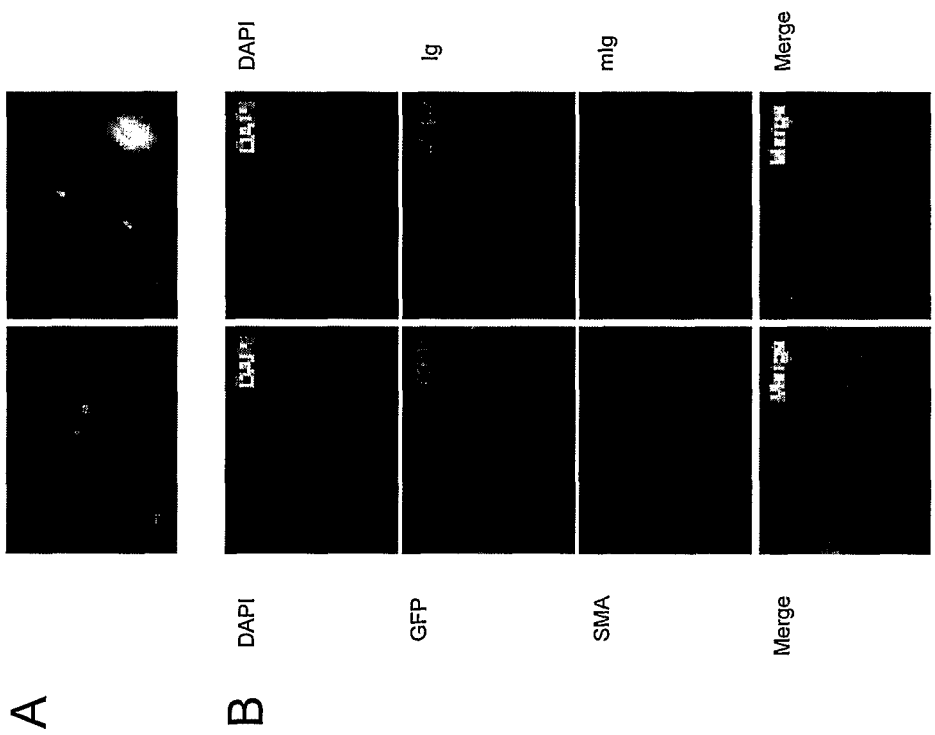
FIG. 8 depicts immunofluorescence images of adoptively transferred GFP-labeled VPC in the setting of balloon injury to the rat carotid artery. 8A depicts two GFP labeled VPC (green cells, left panel) adhering to the lumen of the denuded vessel. Right panel shows a magnified image of a GFP positive VPC attaching to the injured vessel. 8B depicts GFP labeled VPC after injury. DAPI (blue) indicates cell nuclei, GFP labeled VPC are indicated by green, red indicates SMA staining and the merged image shows SMA positive VPC (yellow) in the neointima three weeks post injury.

Adoptively transferred GFP-labeled VPC in the setting of balloon injury to the rat carotid artery were analyzed in vivo. FIG. 8 shows immunofluorescence images. FIG. 8A (left panel) shows two GFP labeled VPC (green cells) adhering to the lumen of the denuded vessel. Right panel shows a magnified image of a GFP positive VPC attaching to the injured vessel. FIG. 8B shows GFP labeled VPC create significant neointima green cells after injury. DAPI (blue) indicates cell nuclei (right and left upper panel), GFP labeled VPC are indicated by green (left upper middle panel, right panel: control), red indicates SMA staining (left lower middle panel, right panel: control) and the merged image shows SMA positive VPC (yellow, left lower panel, right panel: control) in the neointima three weeks post injury.

Example 9

Figure 9:
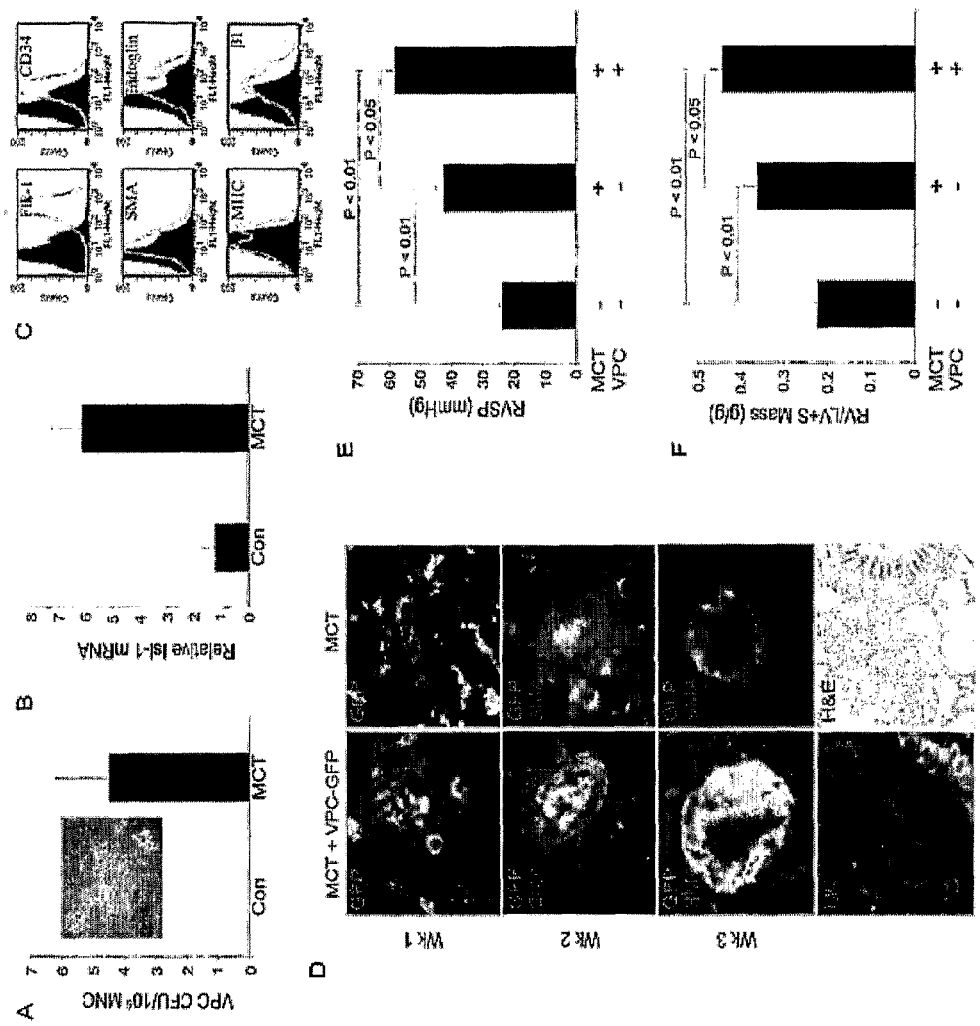
FIG. 9 depicts results showing mobilization of rVPC in peripheral blood 1 week following Monocrotaline (MCT) treatment. 9A depicts a phase image inset showing VPC colony from rat blood outgrowth quantified by histogram. 9B depicts a bar graph showing ISL-1 mRNA levels assessed by quantitative RT-PCR. 9C depicts a FACS profile of rVPC obtained from peripheral blood of MCT treated rats showing immunoreactivity to Flkl, CD34, SMA, CD105, MHC and β1 integrin. 9D depicts immunofluorescence images of adoptively transferred GFP labeled rVPC into syngeneic MCT-treated Fisher rats. Left panel: perivascular collections of GFP labeled rVPC at 1 week in the adoptive transfer group compared to MCT alone control (right panel). Subsequent images show expansion of rVPC in the media of the hypertrophied pulmonary arteries 2 and 3 weeks into the evolution of pulmonary hypertension. 9E depicts a bar graph showing elevation in right ventricular systolic pressure (RVSP), and 9F depicts a bar graph showing right ventricular mass in MCT treated rats (MCT+/VPC−) compared to control treated animals (MCT−/VPC−) and following adoptive transfer of rVPC from syngeneic Fisher rats in the setting of MCT treatment (MCT+/VPC+).

Mobilisation of VPC in peripheral blood 1 week following Monocrotaline (MCT) treatment was analyzed. MCT treatment induces pulmonary hypertension in 3 weeks in rat. The phase image inset of FIG. 9A shows VPC colony from rat blood outgrowth. Histogram shows no VPC colony outgrowth from control rat blood but significant VPC colony numbers from MCT treated rats. ISL-1 mRNA levels were assessed by quantitative RT-PCR. FIG. 9B shows elevation of ISL1 mRNA at 1 week post MCT treatment coinciding with elevation in rat VPC in blood. A FACS profile of VPC obtained from peripheral blood of MCT treated rats shows immunoreactivity to Flk1, CD34, SMA, CD105, MHC and β1 integrin (FIG. 9C). FIG. 9D shows immunofluorescence images of adoptively transferred GFP-labeled VPC into syngeneic MCT-treated Fisher rats. The panels on the left show perivascular collections of GFP labeled VPC at 1 week in the adoptive transfer group compared to MCT alone control (right panels). Subsequent images show expansion of VPC in the media of the hypertrophied pulmonary arteries 2 and 3 weeks into the evolution of pulmonary hypertension. Elevation in right ventricular systolic pressure (RVSP, FIG. 9E) and Right ventricular mass (FIG. 9F) both indicative of pulmonary hypertension in MCT treated rats were compared to control treated animals. Further elevation of both RVSP and RV mass following adoptive transfer of VPC from syngeneic Fisher rats in the setting of MCT treatment was measured.

Example 10

Colony formation and clonal expansion of human PVPC (hVPC) obtained from human bypass filters at time of coronary bypass grafting was assessed.

FIG. 10A-D show clonal expansion of single cell clones to multicellular clusters of lentiviral-GFP transduced hVPC. A and C show phase contrast and B and D immunofluorescence images (GFP) of single cells and VPC clusters. FIG. 10E shows a Southern blot showing identical multi-integration sites of lentivirus following single cell clonal expansion of transduced GFP positive cells during 2nd, 5th and 10th passage in culture.

Example 11

Figure 10:
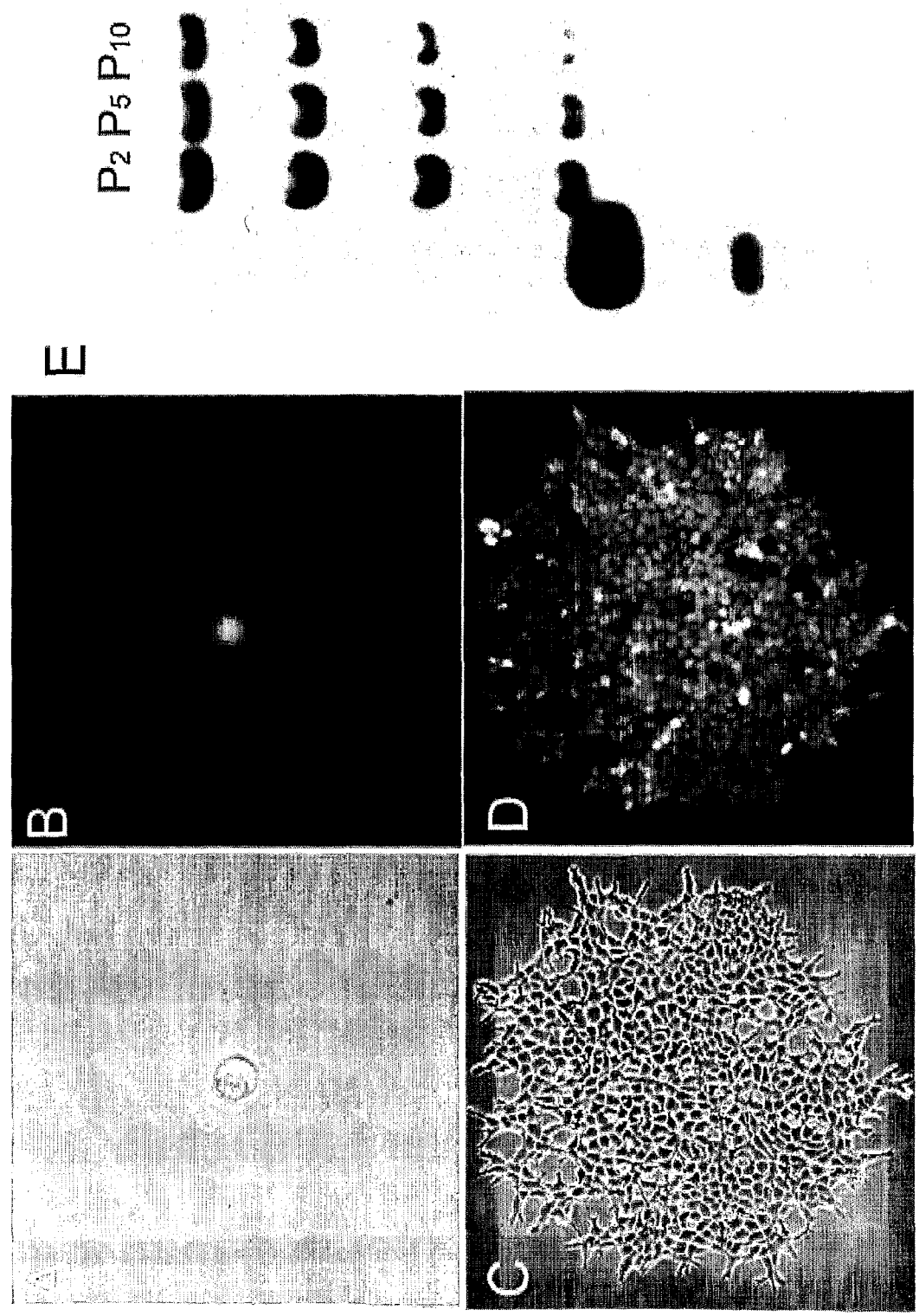
FIG. 10 depicts colony formation and clonal expansion of human VPC (hVPC) obtained from human bypass filters at time of coronary bypass grafting. 10A-D depict phase contrast and immunofluorescent images of clonal expansion of single cell clones to multicellular clusters of lentiviral-GFP transduced hVPC. 10A, C show phase and 10B, D immunofluorescence images of single cells and VPC clusters. 10E depicts a Southern blot showing identical multi-integration sites of lentivirus following single cell clonal expansion of transduced GFP positive cells during 2nd, 5th and 10th passage in culture.
Figure 11:
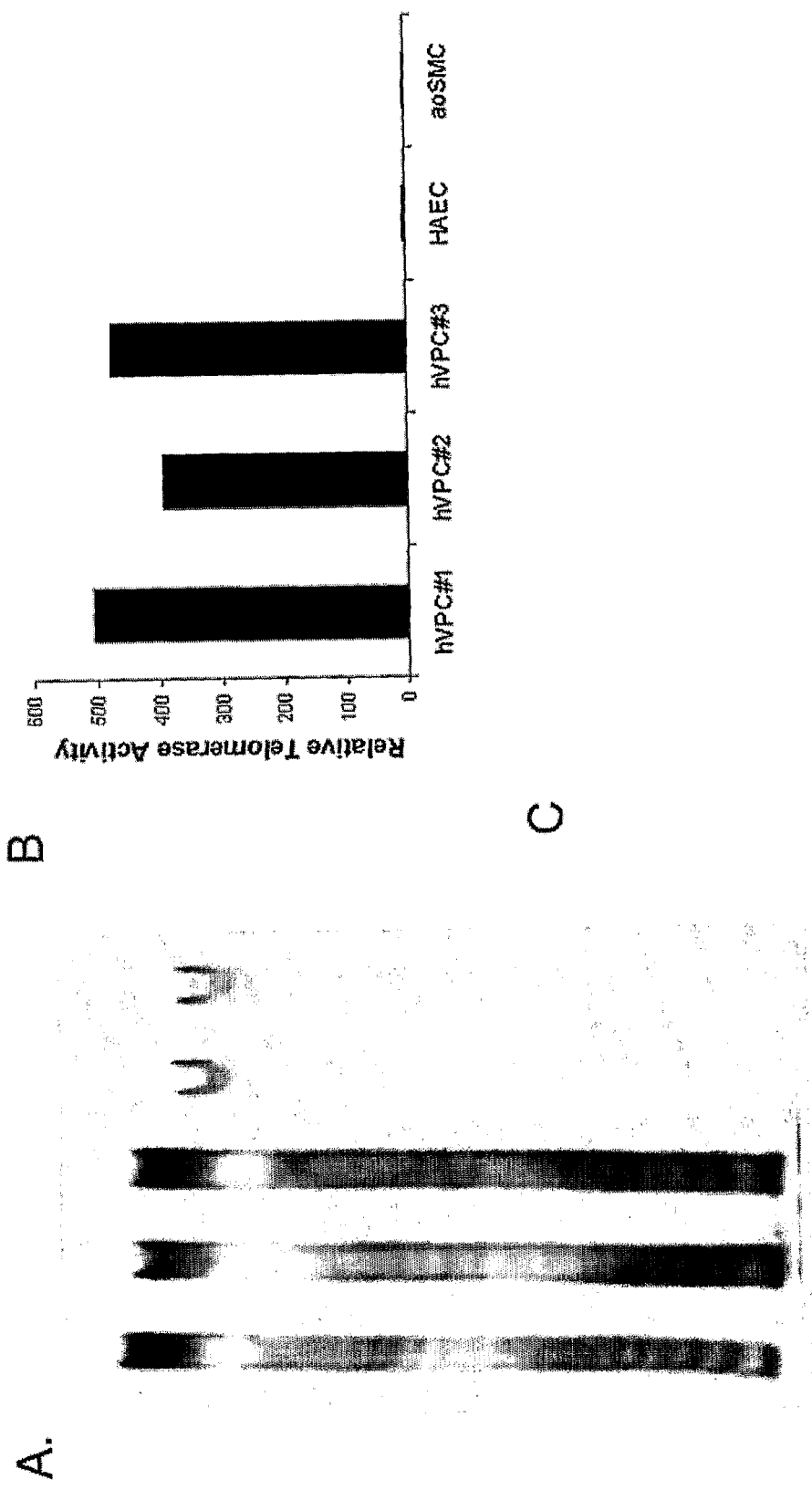
FIG. 11 depicts results showing high telomerase activity in hVPC compared to human aortic endothelial cells (HAEC) and aortic smooth muscle cells (aoSMC) in culture. 11A shows three separate hVPC clones and 11B shows a bar graph quantifying the telomerase activity data.

PVPC (hVPC) show high telomerase activity compared to human aortic endothelial cells (HAEC) and aortic smooth muscle cells (aoSMC) in culture. Three separate hVPC clones (FIG. 11A) and the corresponding telomerase activity FIG. 10B are shown. The control aoSMC or HAEC do not display telomerase activity.

Those skilled in the art will recognize, or be able to ascertain using no more than routine experimentation, many equivalents to the specific embodiments of the invention described herein. Such equivalents are intended to be encompassed by the following claims. All references disclosed herein are incorporated by reference in their entirety.

The invention claimed is:

1. An isolated unipotent mammalian vascular progenitor cell derived from adult mammalian peripheral blood that expresses Isl-1 and Oct4, wherein the vascular progenitor cell has the capacity to differentiate into a smooth muscle cell.

2. An isolated cell of claim 1, wherein the unipotent mammalian vascular progenitor cell further exhibits Flk-1.

3. An isolated cell of claim 1, wherein the unipotent mammalian vascular progenitor cell further exhibits one or more additional markers characteristic of smooth muscle cells and selected from the group consisting of smooth muscle actin (SMA), myosin heavy chain (MHC), calponin, and smoothelin.

4. An isolated cell of claim 1, wherein the unipotent mammalian vascular progenitor cell is capable of exceeding the Hayflick limit of population doublings in vitro, without entering senescence, and/or wherein the cell further exhibits increased telomerase activity compared to a cell not capable of exceeding the Hayflick limit.

* * * * *